United States Patent [19]

Smith et al.

[11] Patent Number: 5,158,597
[45] Date of Patent: Oct. 27, 1992

[54] HERBICIDAL 12-SUBSTITUTED 12H-DIBENZO(D,G)DIOXOCIN-6-CARBOXYLIC ACIDS

[75] Inventors: Michael G. Smith, Walnut Creek; James M. Renga; Brian K. Riley, both of Santa Rosa; Patricia G. Ray, Walnut Creek; Charles Marlowe, San Francisco, all of Calif.

[73] Assignee: The Dow Chemical Company, Midland, Mich.

[21] Appl. No.: 586,165

[22] Filed: Sep. 21, 1990

Related U.S. Application Data

[62] Division of Ser. No. 508,208, Apr. 12, 1990, Pat. No. 4,999,448, which is a division of Ser. No. 366,382, Jun. 15, 1989, Pat. No. 4,938,790.

[51] Int. Cl.$^5$ .............................................. A01N 43/00
[52] U.S. Cl. ........................................ 71/88; 549/336; 549/339; 549/340; 549/349
[58] Field of Search ................... 71/88; 549/349, 336, 549/339, 340

[56] References Cited

U.S. PATENT DOCUMENTS

| 3,553,234 | 1/1971 | Johnson et al. | 549/349 |
| 3,836,543 | 9/1974 | Grisar | 549/349 |
| 3,931,173 | 1/1976 | Parker et al. | 544/148 |

OTHER PUBLICATIONS

J. M. Grisar, et al. *J. Medicinal Chemistry*, 15, 1273–1278 (1972).
H. Linser, *Chemical Abstracts*, 53, 20313f, 1959.
J. L. Fults et al., *Chemical Abstracts*, 42, 1013f&g, 1948.

Primary Examiner—C. Warren Ivy
Assistant Examiner—Amelia A. Owens
Attorney, Agent, or Firm—D. Wendell Osborne

[57] ABSTRACT

Dibenzo[d,g][1,3]dioxocin-6-carboxylic acids substituted by methyl or ethyl or a moiety —CH$_2$CH$_2$— at the 12-position and optionally substituted at other positions, such as methyl 4'-chlorospiro(cyclopropane-1,12'(12'H)-dibenzo[d,g][1,3]dioxocin)-6'-carboxylic acid, and their agriculturally acceptable esters, amides, and salts are useful for the control of undesirable vegetation. The 1,1-diarylcyclopropane intermediates required for the spirocyclopropane compounds can be prepared from appropriately substituted 1,1-diarylethene procursors by reaction with phenylthiomethyl lithium reagent.

18 Claims, No Drawings

HERBICIDAL 12-SUBSTITUTED 12H-DIBENZO(D,G)DIOXOCIN-6-CARBOXYLIC ACIDS

CROSS-REFERENCE TO RELATED APPLICATION

This is a divisional of application Ser. No. 07/508,208 filed on Apr. 12, 1990, now U.S. Pat. No. 4,999,448 which is a divisional of Ser. No. 07/366,382, filed Jun. 15, 1989, now U.S. Pat. No. 4,938,790.

BACKGROUND OF THE INVENTION

The present invention relates to certain dibenzo[d,g][1,3]dioxocin-6-carboxylic acids substituted in the 12-position and, optionally, in other positions and to related compounds that are convertible to substituted dibenzo[d,g][1,3]dioxocin-6-carboxylic acids in the environment or in plants and to the use of these compounds as herbicides.

Certain substituted dibenzo[d,g][1,3]dioxocin-6-carboxylic acids that are unsubstituted at the 12-position and certain of their corresponding esters and amides are known in the art and are reported to possess specific pharmacological utilities. See, for example, U.S. Pat. Nos. 3,931,173 and 3,553,234 and J. *Medicinal Chemistry*, 15, 1273–1278 (1972). Little else is known about this class of compounds.

The production of quality food and fiber is highly dependent on the availability of safe and effective herbicides to control unwanted vegetation. New compounds that are useful in this regard are continuously sought and when found, highly prized.

SUMMARY OF THE INVENTION

It has now been found that substituted dibenzo[d,g][1,3]dioxocin-6-carboxylic acids having hydrocarbyl substitution at the 12-position carbon atom and the salts, esters and amides derived from these acids as well as other related compounds which are chemically or biochemically converted to these acids in the environment or within plants are useful herbicides.

In particular, substituted dibenzo[d,g][1,3]-dioxocin-6-carboxylic acid compounds of Formula I

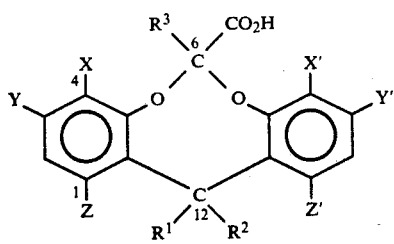

Formula I wherein
$R^1$ and $R^2$ each, independently represent hydrogen, methyl, or ethyl, with the proviso that not more than one of $R^1$ and $R^2$ represents hydrogen, or $R^1$ and $R^2$ together represent the fragment —$CH_2CH_2$—;
$R^3$ represents H or $CH_3$; and
X, X', Y, Y', Z, and Z' each, independently represent H, F, Cl, Br, I, CN, $NO_2$, $CO_2H$, $NH_2$, $C_1$–$C_4$ alkyl, $C_1$–$C_4$ alkoxy, phenoxy, $C_1$–$C_4$ alkylthio, phenylthio, $C_1$–$C_4$ mono- or dialkylamino, ($C_1$–$C_3$ alkyl)carbonyl, or phenylcarbonyl, wherein each alkyl, alkoxy, and alkylthio group is optionally substituted with one or more compatible groups selected from $C_1$–$C_4$ alkoxy, $C_1$–$C_4$ alkylthio, F, Cl, Br, CN, and phenyl and wherein each phenyl group is optionally substituted with up to 3 groups selected from F, Cl, Br, CN, $CF_3$, $C_1$–$C_4$ alkyl, and $C_1$–$C_4$ alkoxy;
and the agriculturally acceptable salt, esters and amides thereof;
and obtainable compounds which are oxidizable or hydrolyzable in plants or the environment to a dibenzo[d,g][1,3]dioxocin-6-carboxylic acid compound of Formula I are useful for the control of undesirable vegetation.

Compositions containing an herbicidally effective amount of a compound of Formula I in admixture with an agriculturally acceptable adjuvant or carrier are usually applied to the undesirable vegetation or the locus thereof in either preemergence or postemergence operations.

The compounds of Formula I wherein $R^1$ and $R^2$ together represent —$CH_2CH_2$— (the moiety —$CR^1R^2$— represents cyclopropylidine) are a generally preferred class. Compounds of Formula I wherein $R^3$ represents hydrogen are also often preferred. Preferred ring substituents include H, F, Cl, Br, $CH_3$, $OCH_3$, $SCH_3$, $CF_3$, and $OC_6H_5$. It is often preferred to employ a compound of Formula I wherein at least one of X and X' represents a designated substituent other than hydrogen.

The invention further embraces a method of preparing a compound of Formula XII

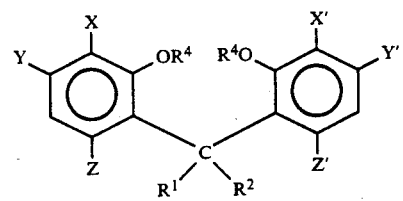

wherein
$R^1$ and $R^2$ together represent the fragment —$CH_2CH_2$—;
each $R^4$ independently represents $C_1$–$C_4$ alkyl optionally substituted with 1 or 2 $C_1$–$C_4$ alkoxy groups; and
X, X', Y, Y', Z, and Z' each, independently represent H, F, Cl, Br, I, CN, $NO_2$, $C_1$–$C_4$ alkyl, $C_1$–$C_4$ alkoxy, phenoxy, $C_1$–$C_4$ alkylthio, phenylthio, or $C_1$–$C_4$ dialkylamino, wherein each alkyl, alkoxy, and alkylthio group is optionally substituted with one or more compatible groups selected from $C_1$–$C_4$ alkoxy, $C_1$–$C_4$ alkylthio, F, Cl, Br, CN, and phenyl and wherein each phenyl group is optionally substituted with up to 3 groups selected from F, Cl, Br, CN, $CF_3$, $C_1$–$C_4$ alkyl, and $C_1$–$C_4$ alkoxy
which comprises contacting thioanisole with a $C_1$–$C_8$ alkyl lithium reagent and an aliphatic tertiary amine in a compatible solvent to form a phenylthiomethyl lithium reagent and subsequently contacting said phenylthiomethyl lithium reagent with a compound of Formula XI

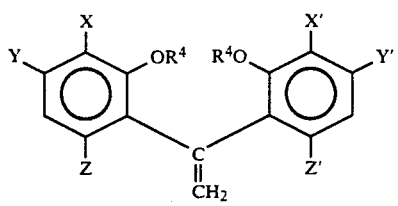

FORMULA XI wherein X, X', Y, Y', Z, and Z' each, independently represent H, F, Cl, Br, I, CN, $NO_2$, $C_1$-$C_4$ alkyl, $C_1$-$C_4$ alkoxy, phenoxy, $C_1$-$C_4$ alkylthio, phenylthio, or $C_1$-$C_4$ dialkylamino, wherein each alkyl, alkoxy, and alkylthio group is optionally substituted with one or more compatible groups selected from $C_1$-$C_4$ alkoxy, $C_1$-$C_4$ alkylthio, F, Cl, Br, CN, and phenyl and wherein each phenyl group is optionally substituted with up to 3 groups selected from F, Cl, Br, CN, $CF_3$, $C_1$-$C_4$ alkyl, and $C_1$-$C_4$ alkoxy under conditions conducive to the reaction.

DETAILED DESCRIPTION OF THE INVENTION

The 12-substituted 12H-dibenzo[d,g][1,3]-dioxocin-6-carboxylic acid compounds of Formula I wherein $R^1$, $R^2$, $R^3$, X, X', Y, Y', Z, and Z' are selected from among the substituents designated in the Summary of the Invention as well as the agriculturally acceptable salts, esters, and amides derived from these acids and all obtainable compounds that are converted to these acids when applied as herbicides are compounds within the scope of the invention. The subject acids are characterized by the presence of a 12H-dibenzo-[d,g][1,3]dioxocin ring system, a carboxylic acid moiety in the 6-position, the presence of at least one hydrocarbon substituent in the 12-position (which substituents may form a carbocycle with the 12-position carbon atom), and the absence of substituents other than hydrogen at the 2- and 10-positions.

The compounds of Formula I possess an asymmetric carbon atom at the 6-position and, whenever $R^2$ and $R^3$ are different, also possess a second asymmetric carbon atom at the 12-position. These compounds, therefore, can exist in several chiral and geometric isomeric forms. Each possible such isomer is described by Formula I and the present invention relates to each of these isomers independently as well as to all mixtures thereof.

The terms alkyl, alkenyl, alkoxy, and alkylthio as used herein include straight chain and branched chain isomers. Thus, typical alkyl groups are methyl, ethyl, 1-methylethyl, 1,1-dimethylethyl, propyl, 2-methylpropyl, 1-methylpropyl, and butyl. Compatible substituents are substituents that are chemically and sterically capable of existing in the designated positions at the same time.

Agriculturally acceptable salts, esters and amides are those salts, esters and amides of the carboxylic acid group(s) of Formula I which have a cation, OR, $NH_2$, NHR, or NRR moiety that is not itself significantly herbicidal to any crop being treated and not significantly deleterious to the applicator, the environment, or the ultimate user of any crop being treated.

Suitable cations include, for example, those derived from alkali or alkaline earth metals and those derived from ammonia and amines. Preferred cations include sodium, potassium, magnesium, and aminium cations of the formula $R^5R^6R^7NH^{\oplus}$ wherein $R^5$, $R^6$, and $R^7$ each, independently represents hydrogen or $C_1$-$C_{12}$ alkyl, $C_3$-$C_{12}$ cycloalkyl, or $C_3$-$C_{12}$ alkenyl, each of which is optionally substituted by one or more hydroxy, $C_1$-$C_8$ alkoxy, $C_1$-$C_8$ alkylthio or phenyl groups, provided that $R^5$, $R^6$, and $R^7$ are sterically compatible. Additionally, any two of $R^5$, $R^6$, and $R^7$ together may represent an aliphatic difunctional moiety containing 1 to 12 carbon atoms and up to two oxygen or sulfur atoms. Salts of the compounds of Formula I can be prepared by treatment of compounds of Formula I with a metal hydroxide, such as sodium hydroxide, potassium hydroxide, or magnesium hydroxide, or an amine, such as ammonia, triethylamine, dimethylamine, hydroxyethylamine, trisallylamine, 2-butoxyethylamine, morpholine, cyclododecylamine, or benzylamine.

Suitable esters and amides include those wherein each R independently represents $C_1$-$C_8$ alkyl or $C_3$-$C_8$ alkenyl, each substituted with up to 3 compatible groups selected from $C_1$-$C_4$ alkoxy, F, Cl, Br, and phenyl, or phenyl optionally substituted with up to 3 groups selected from F, Cl, Br, $CH_3$, or $CF_3$. $C_1$-$C_4$ Alkyl esters are generally preferred and methyl and butyl esters are often specifically preferred.

The nature of the substituents $R^1$, $R^2$, $R^3$, X, X', Y, Y', Z, and Z' within the described limits does not appear to be critical to the general utility of the compounds, but it is a factor in determining the degree of herbicidal activity and the selectivity of the herbicidal action of these compounds. Consequently, some of the compounds are preferred. With respect to $R^1$ and $R^2$, compounds having $R^1$ and $R^2$ together represents the moiety $-CH_2CH_2-$; i.e., compounds wherein the carbon atom at the 12-position is part of a cyclopropylidine moiety, are a preferred sub-set. These compounds are generally termed spiro(cyclopropane-1,12'(12'H)-dibenzo[d,g][1,3]dioxocin)-6'-carboxylates. Other preferred $R^1$ and $R^2$ substituents include methyl. Hydrogen is the preferred $R^3$ substituent. With respect to the ring substituents X, X', Y, Y', Z, and Z', compounds wherein each of these substituents represents hydrogen are often preferred. Compounds wherein at least one of X and X' represents a designated substituent other than hydrogen are also often preferred. Of the substituents designated for X, X', Y, Y', Z, and Z', the following are often preferred: H, F, Cl, Br, $CH_3$, $OCH_3$, $SCH_3$, $CF_3$, and $OC_6H_5$.

The compounds of Table I are illustrative of the compounds of the invention.

SUBSTITUTED DIBENZO[D,G][1,3]DIOXOCIN-6-CARBOXYLIC ACIDS AND ACID FUNCTION DERIVATIVES

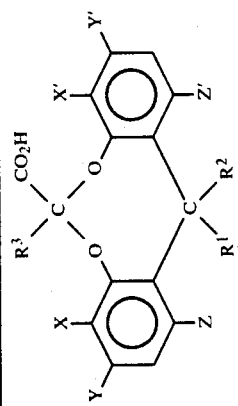

| Cpd. No. | $R^1/R^2$ (isomer) | $R^3$ | X | Y | Z | X' | Y' | Z' | Acid Function Form | Melting Point, °C |
|---|---|---|---|---|---|---|---|---|---|---|
| 1 | CH₃/H (3.7:1) | H | Cl | H | H | H | H | H | methyl ester | 124–136 |
| 2 | CH₃/H (trans) | H | Cl | H | H | H | H | H | methyl ester | 144–145 |
| 3 | CH₃/H (cis) | H | H | H | H | H | H | H | methyl ester | 146–147 |
| 4 | CH₃/H (1:1) | CH₃ | H | H | H | H | H | H | methyl ester | solid |
| 5 | CH₃/H | H | CF₃ | Cl | F | Br | Cl | Br | NHC₁H₇ amide | <50 |
| 6 | CH₃/H | H | Cl | H | H | Cl | H | H | CH₂CH₂OCH₃ ester | 91–92 |
| 7 | CH₃/CH₃ | H | H | H | H | H | H | H | acid | |
| 8 | CH₃/CH₃ | H | H | H | H | H | H | H | methyl ester | |
| 9 | CH₃/CH₃ | CH₃ | CH₃ | H | CN | CH₃ | H | CN | sodium salt | |
| 10 | CH₃/CH₃ | H | I | SCH₃ | H | H | NO₂ | H | C₄H₉ ester | |
| 11 | CH₃/CH₃ | CH₃ | CH₃ | Cl | Cl | CH₃ | Cl | Cl | ammonium salt | |
| 12 | CH₃/CH₃ | CH₃ | F | H | OCH₃ | F | H | CO₂C₂H₅ | CH₂CCl=CCl₂ ester | 123–124 |
| 13 | CH₃/C₂H₅ (95:5) | H | SCH(CH₃)₂ | H | H | H | H | H | acid | 80–85 |
| 14 | CH₃/C₂H₅ (1:1) | H | H | H | H | H | H | H | acid | |
| 15 | CH₃/C₂H₅ | CH₃ | OCF₂CFClH | H | NHCH₃ | OCH₃ | CO₂CH₂CH(OCH₃)CH₂OCH₃ | CH₃ | CO₂CH₂CH(OCH₃)CH₂OCH₃ ester | 142–145 |
| 16 | C₂H₅/H (1:1) | H | H | H | H | H | H | H | acid | 134.5–135.5 |
| 17 | C₂H₅/H (1:1) | H | H | CN | H | CH₃ | H | OCF₂H | methyl ester | 142.5–145 |
| 18 | C₂H₅/C₂H₅ | H | NH₂ | H | H | H | H | H | morpholinium salt | 132–134 |
| 19 | —(CH₂)₂— | H | H | H | H | H | H | H | acid | 114–115 |
| 20 | —(CH₂)₂— | H | H | H | H | H | H | H | methyl ester | 84–87 |
| 21 | —(CH₂)₂— | H | H | H | H | H | H | H | ethyl ester | |
| 22 | —(CH₂)₂— | H | H | H | H | H | H | H | isopropyl ester | |
| $R^1/R^2$ | | | | | | | | | | |
| 23 | —(CH₂)₂— | H | H | H | H | H | H | H | NHOH amide | 127–135(d) |
| 24 | —(CH₂)₂— | H | H | OCH₃ | H | H | H | H | acid | 137–139 |
| 25 | —(CH₂)₂— | H | H | OCH₃ | H | H | H | H | methyl ester | 129–131 |
| 26 | —(CH₂)₂— | H | OCH₃ | H | H | H | H | H | methyl ester | |
| 27 | —(CH₂)₂— | H | OCH₃ | OCH₃ | H | H | H | H | methyl ester | 192–193 |
| 28 | —(CH₂)₂— | H | CH₃ | H | H | H | H | H | acid | 98–99 |
| 29 | —(CH₂)₂— | H | CH₃ | H | H | H | H | H | methyl ester | 154–158 |
| 30 | —(CH₂)₂— | H | Cl | H | H | H | H | H | acid | 105–111 |
| 31 | —(CH₂)₂— | H | Cl | H | H | H | H | H | methyl ester | |

-continued

SUBSTITUTED DIBENZO[D,G][1,3]DIOXOCIN-6-CARBOXYLIC ACIDS AND ACID FUNCTION DERIVATIVES

| Cpd. No. | | R³ | X | Y | Z | X' | Y' | Z' | Acid Function Form | Melting Point, °C. |
|---|---|---|---|---|---|---|---|---|---|---|
| 32 | —(CH₂)₂— | H | CON(CH₃)₂ | H | H | H | H | H | acid | 112-118 |
| 33 | —(CH₂)₂— | H | CON(CH₃)₂ | H | H | H | H | H | methyl ester | 131-134 |
| 34 | —(CH₂)₂— | H | COC₆H₅ | H | H | H | H | H | acid | 183-186 |
| 35 | —(CH₂)₂— | CH₃ | COC₆H₅ | H | H | H | H | H | methyl ester | 135-139 |
| 36 | —(CH₂)₂— | CH₃ | N(CH₃)₂ | OC₂H₅ | Cl | CON(CH₃)₂ | CN | COCF₃ | C₈H₁₇ ester | |
| 37 | —(CH₂)₂— | H | NO₂ | F | CN | H | CF₃ | NH₂ | N(CH₃)₂ amide | |
| 38 | —(CH₂)₂— | H | CO₂C₄H₉ | Br | C₂H₅ | CH(CH₃)₂ | F | S(CH₂)₂CN | (C₂H₅)₃NH⁺ salt | |
| 39 | —(CH₂)₂— | H | H | COC₆H₄Cl | Cl | H | H | H | CH₃(CH₂)₇OCH₂CH₂NH₃⁺ salt | |
| 40 | —(CH₂)₂— | CH₃ | CF₃ | H | H | CF₃ | H | NO₂ | potassium salt | |
| 41 | —(CH₂)₂— | H | OC₄H₉ | CH₃ | H | OC₄H₉ | H | Cl | NH₂ amide | |
| 42 | —(CH₂)₂— | H | H | CH₃ | H | H | CH₃ | H | NHCH₂CO₂CH₃ amide | |
| 43 | —(CH₂)₂— | H | H | CH₃ | H | H | H | H | acid | |
| 44 | —(CH₂)₂— | H | H | H | H | H | H | H | methyl ester | |

Compounds which are obtainable employing the teachings herein, the teachings and suggestions of the prior art, and ordinary skill in the art and which degrade in the environment or within plants to a compound of Formula I will have utilities similar to the compounds of Formula I and the use of such compounds is within the scope of the present invention. Many such compounds can be envisioned. Thus, those compounds which are readily oxidized and/or hydrolyzed in the environment or within a plant system to a compound of Formula I, such as, for example, the 6-hydroxymethyl, 6-aminomethyl, 6-formyl, 6-(2-carboxyethyl), 6-(5-chloro-2-pentenyl), 6-cyano, 6-(2-dioxolanyl), and many other derivatives have approximately the same utility as the compound to which they degrade. The art is replete with other functional groups which are degradable to carboxylic acids, and accordingly, when any of these functional groups is present in place of the $CO_2H$ moiety in the 6-position of a compound of Formula I, a useful herbicide is obtained.

The compounds of the present invention can be prepared in a number of ways. The most general method involves the condensation of a bisphenol compound of Formula II, wherein X, X', Y, Y', Z, Z', $R^1$ and $R^2$ are as defined in the Summary of the Invention, with a 2,2-dihaloalkanoic acid of Formula III, wherein $R^3$ represents hydrogen or methyl and G denotes chloro or bromo; or with an ester or amide of such a 2,2-dihaloalkanoic acid. Dichloroacetic acid is preferred.

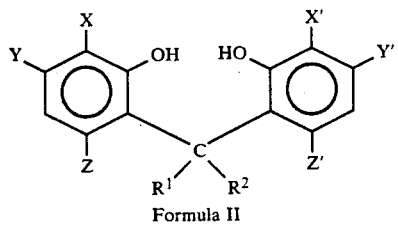 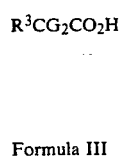

Formula II    Formula III

The process can be carried out essentially as described for related compounds in U.S. Pat. Nos. 3,553,234 and 3,931,173, and J. Med. Chem., 15, 1273-1278 (1972), the appropriate portions of which are hereby incorporated by reference. It is often convenient to reflux a mixture of a compound of Formula II and a compound of Formula III (or an ester or amide thereof) in a solvent with a catalytic amount of potassium iodide for a few days. 2-Propanol is a preferred solvent.

It is generally preferred to do the condensation with an acid of Formula III and, if desired, to subsequently convert the compound of Formula I (acid form) obtained to an agriculturally acceptable ester or amide using standard methods well known to those of ordinary skill in the art. It is sometimes preferred to choose the acid, ester or amide of a compound of Formula III which corresponds to a desired acid, ester or amide of the compound of Formula I to be prepared. In this way the subsequent interconversion or these functionalities to obtain the desired derivative can be avoided.

Alternately, the cyclization can be accomplished by condensation of a bisphenol of Formula II with diethyl dibromomalonate and base. The desired compound of Formula I can be obtained after hydrolysis and decarboxylation of the product prepared, using standard conditions for such reactions. This condensation requires less drastic conditions than the usual method and is valuable for compounds having substituents that are unstable in base, such as trifluoromethyl.

A few compounds of Formula II, wherein $R^1$ and/or $R^2$ represent methyl or ethyl and X, X', Y, Y', Z, and Z' are as defined in the Summary of the Invention, are known in the art. These and other compounds of Formula II can be prepared in a variety of ways. For example, compounds of Formula II wherein one of $R^1$ and $R^2$ represents methyl or ethyl and the other represents hydrogen can be prepared by condensing an appropriate compound of Formula IV wherein R" represents methyl or methoxymethyl and W represents hydrogen or bromo with an appropriate compound of Formula V wherein R' represents methyl, methoxymethyl, or hydrogen and R''' represents methyl or ethyl with an alkyl lithium compound, such as butyl lithium, and subsequently reducing and dealkylating the bis(substituted-phenyl)methanol compound of Formula VI obtained. R" is often preferably methoxymethyl and R' is often preferably methyl. W is usually preferably hydrogen unless X is hydrogen or bromo in which case bromo is usually preferable. The condensation can be carried out by first lithiating the compound of Formula IV with the alkyl lithium at about 0° C. in an ether type solvent, such as tetrahydrofuran, in the presence of a complexing agent, such as tetramethylethylenediamine, and then allowing the lithium compound formed to react with the substituted acetyl or propionyl compound of Formula V under similar conditions. The compound of Formula VI formed can be recovered by adding a saturated aqueous solution of ammonium chloride and extracting with ether.

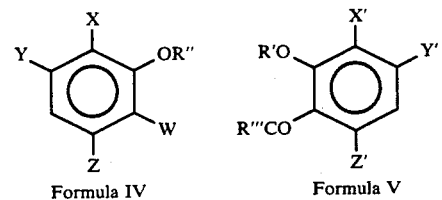

Formula IV    Formula V

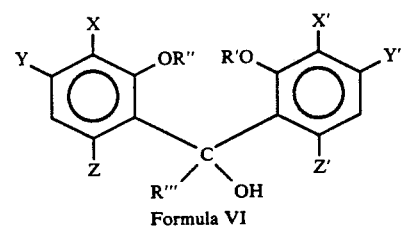

Formula VI

A variety of methods exist for reducing and dealkylating the compounds of Formula VI to compounds of Formula II. It has been found convenient to first reduce the 1,1-bis(substituted-phenyl)alkanol to the corresponding 1,1-bis(substituted-phenyl)alkane with a trialkylsilane and trifluoroacetic acid. Typically, the compound of Formula VI is treated with these reagents in a solvent, such as methylene chloride, at ambient temperature. The product can be recovered by quenching the reaction mixture with saturated aqueous sodium bicarbonate and extracting with ether. The 1,1-bis(substituted-phenyl)alkane thus obtained can be dealkylated (have the R' and R" alkyl groups removed) by most general methods for such reactions. Sometimes, methoxymethyl groups are removed incidentally in the trialkylsilane reduction process. Typically, methoxymethyl groups can be removed by allowing the compounds to react with p-toluene-sulfonic acid in refluxing methanol or by treatment with bromodiethylborane. Methyl groups can be removed by reaction with boron tribromide or bromodimethylborane. Typically, the methoxy containing compound is combined with boron tribromide or bromodimethylborane in a solvent, such as methylene chloride, at ambient temperature to effect the reaction. The resulting compound of Formula II can be recovered by conventional means, such as extraction into aqueous alkali and then adding acid. A large number of the starting material compounds of Formulas IV and V are known in the art or can be made by methods known in the art. Ether compounds of Formula IV are readily prepared from the corresponding phenols of Formula VII by conventional methods.

Alternately, many of the compounds of Formula II can be prepared by condensation of a compound of Formula VII with a compound of Formula VIII using a Grignard reagent, such as ethyl magnesium bromide, in excess. Typically, the condensation is effected by combining the reagents in ether, replacing the ether with benzene after a short period, and heating the latter mixture at reflux for several hours. The compound of Formula II is recovered by conventional techniques for Grignard reactions. A large number of the starting material compounds of Formulas VII and VIII are known in the art or can be made by methods known in the art.

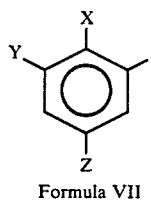
Formula VII

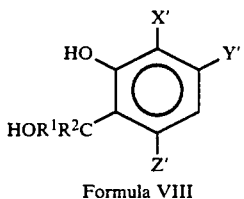
Formula VIII

Other methods exist for the preparation of compounds of Formula II. For example, many dihydroxybenzophenones of Formula IX are known in the art or can be made by methods known in the art and many of these can be converted to compounds of Formula II.

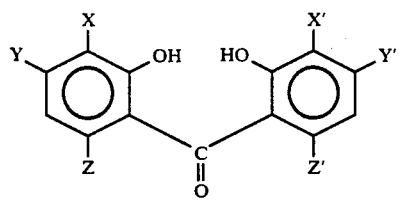
Formula IX

One method of preparation of compounds of Formula IX is by oxidation of a compound of Formula VI wherein R''' represents hydrogen. Such compounds of Formula VI can, in turn, be prepared in the same manner as compounds of Formula VI wherein R''' represents methyl or ethyl by using a compound of Formula V wherein the R''' moiety is replaced by hydrogen. Dipyridine chromic oxide (Collins' reagent) is one suitable oxidizing agent for the transformation. In a typical procedure pyridine and chromic oxide are combined at about 0° C. and then an appropriate compound of Formula VI is added and the mixture allowed to react at or below ambient temperature for several hours. The desired product can be recovered by conventional means.

Compounds of Formula II wherein one of $R^1$ and $R^2$ represents methyl or ethyl and the other represents hydrogen can be prepared from compounds of Formula IX by alkylation with methyl or ethyl magnesium bromide in ether under typical Grignard reaction conditions to obtain a compound of Formula VI. The product can be recovered using typical Grignard reaction work-up procedures. The compound of Formula VI can then be reduced and dealkyated as described here-in-above to obtain the desired compound of Formula II.

Compounds of Formula II wherein both $R^1$ and $R^2$ represent methyl or ethyl or together $R^1$ and $R^2$ represent the moiety —$CH_2CH_2$— can be prepared from compounds of Formula IX by first converting the compound of Formula IX to a compound of Formula X

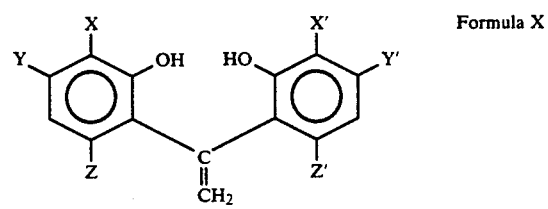
Formula X

This can be accomplished by treating the compound of Formula IX with methyl magnesium bromide to obtain a 1,1-bis(substituted-phenyl)ethanol (compound of Formula VI wherein R''' represents methyl) as described above and then dehydrating this compound. Compounds of Formula VI obtained by other means are, of course, equally employed. The dehydration can be carried out, for example, by heating the compound of Formula VI in acetic anhydride containing a catalytic amount of sulfuric acid and recovering the product of Formula X by conventional means. An ethylidene analog ($CH_2=$ replaced by $CH_3CH=$) can be prepared by substituting ethyl magnesium bromide for methyl magnesium bromide in the procedure. The method proceeds at least equally as well when the dimethyl ether of a compound of Formula IX is employed as the substrate and the dimethyl ether of the corresponding compound of Formula X is obtained. Alternately, the alkyl ether derivatives of compounds of Formula X can be prepared by treatment of the dialkyl ether derivatives of compounds of Formula IX with methyltriphenylphosphonium bromide and sodium hydride in tetrahydrofuran, an application of the well-known Wittig reaction. The desired intermediates of Formula X can also be prepared by allowing a bis(methoxymethyl) ether derivative of a compound of Formula IX to react in tetrahydrofuran first with trimethylsilylmethyl lithium and then with potassium t-butoxide to obtain a bis(methoxymethyl) ether derivative of a compound of Formula X and subsequently removing the methoxymethyl protecting groups with a standard reagent, such as methanol containing a catalytic amount of p-toluenesulfonic acid. This is often a preferred method.

The dimethyl ether analogs of the compounds of Formulas IX and X can be prepared from compounds of Formulas IX and X, respectively, for example, by treatment with methyl iodide and a base under conditions well known in the art. The bis(methoxymethyl) ether analogs can also be prepared by conventional procedures, which generally employ dimethoxymethane and an acid catalyst. Demethylation of the dimethyl ether analogs of compounds of Formulas II, IX, and X and the like can be accomplished by treatment with boron tribromide, bromodimethylborane or any of the other suitable reagent known in the art. De(methoxymethylation) of the bis(methoxymethyl) ether analogs of these compounds can be accomplished with the same reagents as well as with milder reagents, such as benzenesulfonic acid in methanol.

Compounds of Formula II wherein one of $R^1$ and $R^2$ represents ethyl and the other represents methyl or ethyl can be prepared from compounds of Formula X by treatment of the dimethyl ether derivatives of these compounds with methyl lithium and then methyl or ethyl bromide. The methyl lithium is generally added to a solution of the reactant in tetrahydrofuran and after a 1 to 4 hour period the alkyl iodide is added slowly. The dimethyl ether analog of the desired compound of Formula X can be recovered by conventional means. It can be converted to a compound of Formula X by demethylation using standard methods.

Compounds of Formula XII

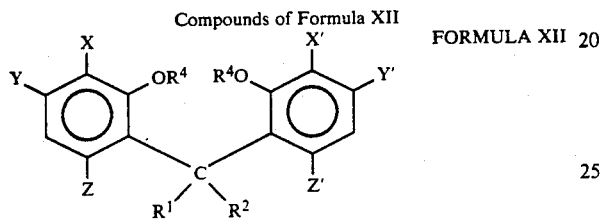

FORMULA XII wherein $R^1$ and $R^2$ together represent the moiety —$CH_2CH_2$— (the moiety bridging the two benzene rings is a cyclopropylidine moiety) and wherein each $R^4$ independently represents $C_1$-$C_4$ alkyl optionally substituted with 1 or 2 $C_1$-$C_4$ alkoxy groups and X, X', Y, Y', Z, and Z' each, independently represent H, F, Cl, Br, I, CN, $NO_2$, $C_1$-$C_4$ alkyl, $C_1$-$C_4$ alkoxy, phenoxy, $C_1$-$C_4$ alkylthio, phenylthio, or $C_1$-$C_4$ dialkylamino, wherein each alkyl, alkoxy, and alkylthio group is optionally substituted with one or more compatible groups selected from $C_1$-$C_4$ alkoxy, $C_1$-$C_4$ alkylthio, F, Cl, Br, CN, and phenyl and wherein each phenyl group is optionally substituted with up to 3 groups selected from F, Cl, Br, CN, $CF_3$, $C_1$-$C_4$ alkyl, and $C_1$-$C_4$ alkoxy can be prepared from a compound of Formula XI,

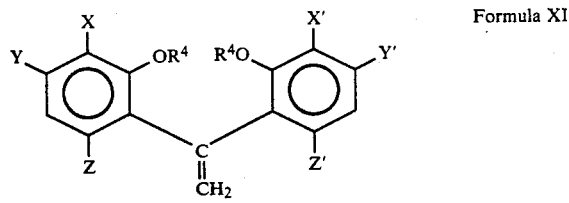

Formula XI wherein the substituents are defined in the same way, by treatment with phenylthiomethyl lithium.

A solution of phenylthiomethyl lithium in a compatible solvent, such as pentane, decane or another aliphatic hydrocarbon solvent or tetrahydrofuran, dimethoxyethane, diethyl ether or another ether type solvent, is generally first prepared by adding an alkyl lithium reagent, such as butyl lithium, to a solution of thioanisole (methylthiobenzene) and an aliphatic tertiary amine, such as 1,4'-diazabicyclo[2,2,2]octane, in a compatible solvent. Approximately equimolar amounts of each of the reactants are employed although this is not critical. The mixture is generally cooled to around 0° C. and the reaction allowed to proceed at temperatures up to about 30° C. The reaction is generally complete in less than one hour. The phenylthiomethyl lithium reagent prepared is generally combined with an approximately equimolar or lesser amount of a compound of Formula XI in a compatible solvent. The combination can be made over a wide range of temperatures and is often most conveniently carried out at about ambient temperature. The mixture is then generally heated to complete the conversion. Temperatures of about 30° C. to about 100° C. or the reflux temperature of the mixture are typically employed and the reaction is generally complete within 24 hours after the temperature is elevated. The desired product of Formula XII (a bisether derivative of a compound of Formula II wherein $R^1$ and $R^2$ together represent the moiety —$CH_2CH_2$—) can be recovered by conventional means. It is often readily recovered by quenching with water, separating the aqueous phase that forms, extracting the organic phase with more water, distilling the organic phase under reduced pressure to remove the volatile organics, and chromatographing the residue. Compounds of Formula II wherein $R^1$ and $R^2$ together represent the moiety —$CH_2CH_2$— can be obtained from the compounds prepared in the process described above by dealkyation using standard methods. A compatible solvent is one that dissolves at least a small amount of each reactant and which is chemically inert in the system.

It is also possible to obtain compounds of Formula XII wherein $R^1$ and $R^2$ together represent the moiety —$CH_2CH_2$— from appropriate bisether derivatives of the compounds of Formula IX by treatment with triethyl phosphonoacetate and sodium hydride in an ether solvent, such as dimethoxyethane, followed by treatment of the intermediate obtained with lithium aluminum hydride in an ether solvent. The triethyl phosphonoacetate and sodium hydride are generally first combined and allowed to react and then the bisether derivative of a compound of Formula IX is added and the mixture heated for about a day. An intermediate product can be recovered by adding water and isolating the organic phase. This intermediate, in crude or purified form, is then generally added to lithium aluminum hydride in tetrahydrofuran and the mixture heated at reflux for several hours. The expected product is recovered by conventional means for such reactions. The procedure is similar to that described in *Organic Synthesis*, Collective Volume V, pp 509–510. The desired compound of Formula II is obtained by dealkylation of the ether substituents by conventional means.

The choice of a method to use in the preparation of the desired compound of Formula II will depend on the availability of starting materials, the sensitivity of the substituents to the reaction conditions that will be employed in subsequent reactions, and the possibility of isomer formation which would make recovery of the desired product difficult. Protecting groups, such as t-butyl and trimethylsilyl, can be employed in the process and subsequently removed as is known in the art.

It is not always necessary to prepare a compound of Formula II to obtain the corresponding compound of Formula I. It is often possible and desirable to prepare certain compounds of Formula I by converting one compound of Formula I (or a related compound with a substituent pattern not covered by Formula I) prepared as described herein or obtained in another manner to another compound of Formula I using convention chemical methods. Thus, for example, a t-butyl group can be used as a protecting group and removed by treatment with aluminum chloride, a bromo or iodo substituent can be removed with a reducing agent or replaced by other groups by nucleophilic displacement, such as with cuprous cyanide, a nitro group can be reduced to an amino group, a trialkylsilyl group can be replaced by bromo or iodo, and a methoxy group can be converted to a hydroxy group with an alkanethiol and base. An hydroxy group can further be alkylated by known methods to alkoxy groups, including substituted alkoxy groups as defined in the Summary of the Invention. Such transformations are well known to those in the art.

It is further possible to prepare compounds of Formula I from compounds of Formula IX by first condensing the latter with a compound of Formula III in the same manner employed in the reaction of compounds of Formula II with compounds of Formula III and then appropriately modifying the 12-oxo analog of the compound of Formula I obtained by the general methods described herein or otherwise known in the art.

Compounds of Formula I wherein $R^3$ represents methyl are usually best prepared by methylation of a compound of Formula I wherein $R^3$ represents hydrogen. In typical operations a compound of Formula I wherein R represents hydrogen is added dropwise with stirring to a solution of an alkyl lithium compound, such as butyl lithium, and diisopropylamine in a solvent, such as tetrahydrofuran, while cooling with dry-ice and acetone to about $-78°$ C. and after a few minutes adding excess methyl iodide. The 6-methyl compound can be recovered be conventional means, for example, by adding dilute aqueous hydrochloric acid and then extracting with ether.

The compounds of the present invention can be used directly as herbicides, but it is generally preferable to first prepare a herbicidal composition containing one or more of the compounds in combination with an agriculturally acceptable adjuvant or carrier. Suitable adjuvants or carriers should not be phytotoxic to valuable crops, particularly at the concentrations employed in applying the compositions for selective weed control in the presence of crops, and should not react chemically with compounds of Formula I or other composition ingredients. Such mixtures can be designed for application directly to plants or their locus or can be concentrates or formulations which are normally diluted with additional carriers and adjuvants before application. They can be solids, such as, for example, dusts, granules, water dispersible granules, or wettable powders, or liquids, such as, for example, emulsifiable concentrates, solutions, emulsions or suspensions.

Suitable agricultural adjuvants and carriers that are useful in preparing the herbicidal mixtures of the invention are well known to those skilled in the art.

Liquid carriers that can be employed include water, toluene, xylene, petroleum naphtha, crop oil, acetone, methyl ethyl ketone, cyclohexanone, trichloroethylene, perchloroethylene, ethyl acetate, amyl acetate, butyl acetate, propylene glycol monomethyl ether and diethylene glycol monomethyl ether, isopropyl alcohol, amyl alcohol, ethylene glycol, propylene glycol, glycerine, and the like. Water is generally the carrier of choice for the dilution of concentrates.

Suitable solid carriers include talc, pyrophyllite clay, silica, attapulgus clay, kieselguhr, chalk, diatomaceous earth, lime, calcium carbonate, bentonite clay, Fuller's earth, cotton seed hulls, wheat flour, soybean flour, pumice, wood flour, walnut shell flour, lignin, and the like.

It is frequently desirable to incorporate one or more surface-active agents into the compositions of the present invention. Such surface-active agents are advantageously employed in both solid and liquid compositions, especially those designed to be diluted with carrier before application. The surface-active agents can be anionic, cationic or nonionic in character and can be employed as emulsifying agents, wetting agents, suspending agents, or for other purposes. Typical surface active agents include salts of alkyl sulfates, such as diethanolammonium lauryl sulfate; alkylarysulfonate salts, such as calcium dodecylbenzenesulfonate; alkylphenol-alkylene oxide addition products, such as nonylphenol-C18 ethoxylate; alcohol-alkylene oxide addition products, such as tridecyl alcohol-C16 ethoxylate; soaps, such as sodium stearate; alkylnaphthalenesulfonate salts, such as sodium dibutylnaphthalenesulfonate; dialkyl esters of sulfosuccinate salts, such as sodium di(2-ethylhexyl) sulfosuccinate; sorbitol esters, such as sorbitol oleate; quaternary amines, such as lauryl trimethylammonium chloride; polyethylene glycol esters of fatty acids, such as polyethylene glycol stearate; block copolymers of ethylene oxide and propylene oxide; and salts of mono and dialkyl phosphate esters.

Other adjuvants commonly utilized in agricultural compositions include antifoam agents, compatibilizing agents, sequestering agents, uv absorbers, neutralizing agents and buffers, corrosion inhibitors, dyes, odorant, penetration aids, spreading agents, sticking agents, dispersing agents, thickening agents, freeze point depressants, antimicrobial agents, and the like. The addition of crop oil and crop oil concentrates is typical. The compositions can also contain other compatible components, for example, other herbicides, plant growth regulants, fungicides, insecticides, and the like and can be formulated with solid, particulate fertilizer carriers such as ammonium nitrate, urea and the like or with liquid fertilizers.

The concentration of the active ingredients in the herbicidal compositions of this invention is generally from about 0.001 to about 98 percent by weight. Concentrations from about 0.01 to about 90 percent by weight are often employed. In compositions designed to be employed as concentrates, the active ingredient is generally present in a concentration from about 5 to about 98 weight percent, preferably about 10 to about 90 weight percent. Such compositions are typically diluted with an inert carrier, such as water, before application. The diluted compositions usually applied to plants or their locus generally contain about 0.001 to about 5 weight percent active ingredient and preferably contain about 0.01 to about 1.0 percent The present compositions can be applied by the use of conventional ground or aerial dusters and sprayers, by addition to irrigation water, and by other conventional means known to those skilled in the art.

General herbicide action is usually observed for compounds of Formula I at rates of greater than about 300 g/Ha for either preemergence or postemergence applications. Selective control of susceptible weeds in crops, such as cotton, soybeans, corn, rice, or wheat can be accomplished with certain of the compounds at application rates of about 2 g/Ha to about 500 g/Ha. An appropriate rate for each crop, compound and circumstance can be determined by simple range finding tests using the teachings herein.

The term "herbicide" is used herein to mean an active ingredient which controls or adversely modifies growth of plants. By "vegetation controlling" or "herbicidally effective" amount is meant an amount of active ingredient which causes an adversely modifying effect and includes deviations from natural development, killing, regulation, dessication, retardation, and the like. The terms "plants" and "weeds" are meant to include germinant seeds, emerging seedlings and established vegetation. "Undesirable vegetation" is plant life present in a place where it is not wanted.

Herbicidal activity is exhibited by the compounds of the present invention when they are applied directly to the plant or to the locus of the plant at any stage of growth or before emergence. The effect observed depends upon the plant species to be controlled, the stage of growth of the plant, the application parameters of dilution and spray drop size, the particle size of solid components, the environmental conditions at the time of use, the specific compound employed, the specific adjuvants and carriers employed, and the like, as well as the amount of chemical applied. These and other factors can be adjusted as is known in the art to promote selective herbicidal action.

EXAMPLES

Example 1

Preparation of 1,1-bis(2-methoxyphenyl)-cyclopropane

Sodium hydride (4.4 g of 60 percent oil dispersion) was placed in a flask with 140 ml of dimethoxyethane. This mixture was cooled with an ice bath and 22.3 g of triethyl phosphonoacetate was added dropwise with stirring over a 30 min period. A murky yellow solution was obtained. 2,2'-Dimethoxybenzophenone (20.2 g) was added and the resulting mixture was heated at reflux with stirring for 20 hours. It was then allowed to cool to ambient temperature and was diluted with 500 ml of ether. The resulting mixture was washed with 3–200 ml portions of 1N hydrochloric acid and with saturated sodium bicarbonate, dried over magnesium sulfate, filtered, and concentrated by evaporation under reduced pressure to obtain a turbid, viscous yellow oil. This material was found by gas chromatagraphy to be about 79 percent one compound. It was dissolved in 100 ml of tetrahydrofuran and the solution added dropwise with stirring to a slurry of 4.70 g of lithium aluminum hydride in 100 ml of tetrahydrofuran over a 40 min period. An exothermic reaction ensued. The mixture was heated at reflux for 3 hours and allowed to stand at ambient temperature overnight. About 100 ml of 10 percent sulfuric acid was added carefully with stirring to quench the excess lithium aluminum hydride. About 700 ml of ether was then added and the layers were separated. The ether layer was extracted with water, 10 percent hydrochloric acid, 10 percent potassium hydroxide, and brine. It was then dried over magnesium sulfate, filtered, and concentrated by evaporation under reduced pressure. The residue was purified by filtration chromatography on silica eluting with a 10:90 mixture of ether and hexane. The solvents were removed by evaporation under reduced pressure to obtain 5.6 g (26 percent of theory) of the title compound as pale yellow crystals melting at 146°–149° C. The carbon-13 and proton nmr spectra were in agreement with the assigned structure.

Elemental analysis: Calc. for $C_{17}H_{18}O_2$: % C, 80.3; % H, 7.13. Found: % C, 79.9; % H, 7.02.

Example 2

Preparation of 1,1-Bis(2-hydroxyphenyl)cyclopropane 1,1-Bis(2-methoxyphenyl)cyclopropane (10.0 g, 0.039 mole) was combined with 60 ml of dichloromethane and the mixture was cooled in an ice bath and then treated with 10.0 ml of bromodimethylborane with cooling and stirring. The starting material was consumed in less than 1 hour as determined by gas-liquid chromatography. The mixture was then diluted with 500 ml of ether and the resulting solution was extracted twice with water and then with water saturated with ammonium chloride, dried over magnesium sulfate, filtered, and concentrated by evaporation under reduced pressure to obtain 9.0 g (101 percent of theory) of the title compound as a brownish-black solid; m.p., 158°–160° C. This eluted as one clean peak in gas-liquid chromatography and had a proton NMR spectrum consistent with the assigned structure.

Elemental analysis: Calc. for $C_{15}H_{14}O_2$: % C, 79.6; % H, 6.21. Found: % C, 79.0; % H, 6.21.

2,2-Bis(2-hydroxyphenyl)butane was prepared in the same manner from 2,2-bis(2-methoxyphenyl)-butane. The proton NMR and infrared spectra were consistent with the assigned structure.

Example 3

Preparation of Spiro(cyclopropane-1,12'(12'H)-dibenzo[d,g][1,3]diox-ocin)-6'-carboxylic Acid An 18.5 g (0.082 mole) sample of unpurified 1,1-bis(2-hydroxyphenyl)cyclopropane was combined with 44.0 g (0.32 mole) of potassium carbonate, 2.0 g (0.012 mole) of potassium iodide, 8.0 ml of dichloroacetic acid, and 400 ml of isopropyl alcohol. The mixture was heated at reflux with stirring for 24 hours. Another 8.0 ml of dichloroacetic acid was added and the mixture heated at reflux with stirring for another 48 hours. The volatiles were then removed by evaporation under reduced pressure. The solid that remained was dissolved in 300 ml of water. The resulting solution was extracted with 500 ml of ether, acidified with concentrated hydrochloric acid (carefully due to foaming), and then extracted with three 500 ml portions of ether. The latter ether extracts were dried over magnesium sulfate, filtered, and concentrated under reduced pressure to obtain the title compound in crude form as a solid.

A purified sample of the title compound was obtained by hydrolysis of its methyl ester from Example 4. A 0.070 g sample was dissolved in 10 ml of methanol containing 3 ml of 10 percent aqueous potassium hydroxide and the solution allowed to stir overnight. The mixture was then diluted with 10 ml of water and the resulting solution extracted with 50 ml of ether. The aqueous solution was acidified with 10 percent hydrochloric acid and then extracted with ether. The ether extract was dried over magnesium sulfate, filtered, and concentrated by evaporation under reduced pressure to obtain a solid. This was recrystallized from a 1:1 mixture of chloroform and hexane to obtain 0.33 g of the title compound as a white power melting at 142.5°–145° C. The proton NMR and infrared spectra were consistent with the assigned structure.

Elemental analysis: Calc. for $C_{17}H_{14}O_4$: % C, 72.3; % H, 5.00. Found: % C, 72.3; % H, 4.79.

Example 4

Preparation of Methyl Spiro(cyclopropane-1,12'(12'H)-dibenzo[d,g][1,3]dioxocin)-6'-carboxylate The crude spiro(cyclopropane-1,12'(12'H)-dibenzo[d,g][1,3]dioxocin)-6'-carboxylic acid from Example 3 was dissolved in 500 ml of methanol and 2.0 ml of sulfuric acid added. The mixture was heated at reflux and stirred for 3 hours. About half of the methanol was removed by evaporation under reduced pressure and the remaining solution was diluted with 1.5 l of ether. The solution obtained was extracted several times with water and then with brine and was then dried over magnesium sulfate, filtered, and concentrated by evaporation under reduced pressure to obtain the title compound in impure form. This was purified by filtration chromatography, eluting with a 9:1 mixture of hexane and ether to obtain the product as a pale yellow crystalline solid. This was recrystallized from methanol to obtain 9.55 g of the title compound as pale tan crystals melting at 123°–126° C. The proton and carbon NMR and infrared spectra were consistent with the assigned structure.

Elemental analysis: Calc. for $C_{18}H_{16}O_4$; % C, 73.0; % H, 5.40. Found: % C, 72.9; % H, 5.41.

Example 5

Preparation of 2-Propyl Spiro(cyclopropane-1,12'(12'H)-dibenzo[d,g][1,3]dioxocin)-6'-carboxylate.

Methyl spiro(cyclopropane-1,12'(12'H)-dibenzo[d,g][1,3]dioxocin)-6'-carboxylate (0.60 g) was dissolved in 30 ml of 2-propanol and a trace of sodium methoxide was added. The mixture was allowed to stir until ester interchange was complete as determined by gas-liquid chromatography. The solution was diluted with 150 ml of ether and the resulting solution was extracted several times with water, dried over magnesium sulfate and concentrated by evaporation under reduced pressure to obtain 0.38 g of the title compound as a white crystalline product melting at 84°–87° C. The proton and carbon NMR and infrared spectra were consistent with the assigned structure.

Elemental analysis: Calc. for $C_{20}H_{20}O_4$: % C, 74.1; % H, 6.21. Found: % C, 74.5; % H, 6.24.

the ethyl ester was obtained in the same manner substituting ethanol for 2-propanol and was found to be pale yellow crystals melting at 114°–115° C. The proton and carbon NMR and infrared spectra were consistent with the assigned structure.

Elemental analysis: Calc. for $C_{19}H_{18}O_4$: % C, 73.5; % H, 5.84. Found: % C, 74.2; % H, 5.80.

Example 6

Preparation of Spiro(cyclopropane-1,12'(12'H)-dibenzo[d,g][1,3]dioxocin)-6'-carboxamic Acid Methyl spiro(cyclopropane-1,12'(12'H)-dibenzo[d,g][1,3]dioxocin)-6'-carboxylate (1.30 g), hydroxylamine hydrochloride (1.03 g), sodium methoxide (0.74 g) and 25 ml of methanol were combined and heated to reflux with stirring. After a brief period, the heat was removed and the mixture allowed to stir at ambient temperature overnight. Ether (150 ml) was added and the resulting solution was extracted with dilute hydrochloric acid, water (several times) and finally with saturated aqueous ammonium chloride. The ethereal solution was then dried over magnesium sulfate, filtered, and concentrated by evaporation under reduced pressure to obtain the title compound as a fluffy white solid. This was recrystallized from ethyl acetate/hexane to obtain a 0.52 g first crop and a 0.20 g second crop of the title compound as a fine white powder melting at 127°–135° C. with decomposition. The proton NMR and infrared spectra were consistent with the assigned structure.

Elemental analysis: Calc. for $C_{17}H_{15}NO_4$ % C, 68.7; % H, 5.09; % N, 4.71. Found: % C, 67.8; % H, 5.29; % N, 4.32.

Example 7

Preparation of 1,1-Bis(2-methoxyphenyl)ethanol 2,2'-Dimethoxybenzophenone (24.2 g, 0.14 mole) and 400 ml of ether were placed in a 1 l flask and stirred at ambient temperature and methyl magnesium bromide (40 ml of 3.0M solution in ether) was added dropwise. The resulting mixture was stirred overnight and then a few ml of water were added to quench the Grignard reagent. About 300 ml of ethyl acetate and 250 ml of 10 percent hydrochloric acid were then added and the mixture was shaken. The organic layer was next recovered, extracted with 100 ml of water and 100 ml of saturated sodium bicarbonate, dried over magnesium sulfate, filtered, and concentrated by evaporation under reduced pressure to obtain 25.6 g (98 percent of theory) of the title compound as a white solid melting at 122°–123° C. The proton NMR spectrum was consistent with the assigned structure.

Example 8

Preparation of 1,1-Bis(2-methoxyphenyl)-ethene.

1,1-Bis(2-methoxyphenyl)ethanol (25.6 g) was combined with 250 ml of acetic anhydride and the mixture was heated at reflux for 4 hours. A drop of concentrated sulfuric acid was added and the heating continued for 10 min. The opaque brown mixture obtained was allowed to cool and was diluted with ether. The resulting solution was extracted twice with water, dried over magnesium sulfate, filtered, and concentrated by evaporation under reduced pressure to obtain a brownish-black solid. This was recrystallized from methanol to obtain 14.0 g of the title compound as tan crystals melting at 88°–90° C. The proton NMR spectrum was consistent with the assigned structure.

Elemental analysis: Calc. for $C_{17}H_{15}O_4$ % C, 80.0; % H, 6.71. Found: % C, 79.9; % H, 6.68.

Example 9

Preparation of 2,2-Bis(2-methoxyphenyl)-propane.

1,1-Bis(2-methoxyphenyl)ethene (15.6 g), toluene (35 ml) and anisole (35 ml) were combined in a flask and 35 ml of a 3.7M hexane solution of Red-Al was added. The mixture was heated to reflux with stirring whereupon it turned dark red. After 2 hours the heat was removed and the mixture was allowed to stir overnight. The excess hydride reagent was carefully quenched with 1.0N hydrochloric acid. The mixture was then diluted with ether and the ethereal solution separated, dried over magnesium sulfate, filtered, and concentrated by evaporation under reduced pressure to obtain a golden-brown oil. This was triturated with hexane to obtain 3.70 of the title compound. The proton and carbon NMR spectra were consistent with the assigned structure.

Elemental analysis: Calc. for $C_{17}H_{15}O_4$ % C, 79.7; % H, 7.81. Found: % C, 79.6; % H, 7.86.

A second crop amounting to 2.45 g was obtained by adding methanol.

Example 10

Preparation of 2,2-Bis(2-hydroxyphenyl)propane

Sodium hydride (2.60 g of 60 percent dispersion in oil) was placed in a 1 l flask and extracted twice with pentane. To this was added first 250 ml of dimethylformamide and then, dropwise with stirring over 1 hour, 6.0 ml of ethanethiol in 40 ml of dimethylformamide. 2,2-Bis(2-methoxyphenyl)propane (8.0 g, 31 mmol) in 100 ml of dimethylformamide was then added and the mixture was heated at reflux with stirring for 24 hours and allowed to stand at ambient temperature for another approximately 18 hours. One l of ether was added and the resulting solution was extracted with water and twice with 4.0N sodium hydroxide solution. The combined aqueous extracts were neutralized with concentrated hydrochloric acid to a pH of about 9–10. Ether (500 ml) was then added and, after shaking, the ether layer was separated, dried over magnesium sulfate, filtered, and concentrated by evaporation under reduced pressure to obtain about 3 g of the title compound as a brown oil containing some dimethylformamide. The proton NMR spectrum was consistent with the assigned structure.

Example 11

Preparation of 12,12-Dimethyl-12H-dibenzo[d,g][1,3]dioxocin-6-carboxylic Acid and Methyl 12,12-Dimethtyl-12H-dibenzo[d,g][1,3]dioxocin-6-carboxylate.

2,2-Bis(2-hydroxyphenyl)propane (3 g of unpurified), potassium carbonate (6.5 g), potassium iodide (0.67 g) and dichloroacetic acid (1.0 ml at first, then another 1.2 ml) were combined in isopropyl alcohol and treated as in Example 3 to obtain the title acid in impure form. This was esterified by the procedure of Example 4 to obtain the methyl ester. The methyl ester obtained was purified by column chromatography on silica gel, eluting with an 85:15 mixture of hexane and ether, and then by recrystallization from ether-pentane to obtain 0.45 g of the title methyl ester compound as white crystals melting at 91°–92° C. The proton NMR and infrared spectra were consistent with the assigned structure.

Elemental analysis: Calc. for $C_{18}H_{18}O_4$: % C, 72.5; % H, 6.08. Found: % C, 72.4; % H, 5.87.

A sample of the methyl ester was hydrolyzed as in Example 3 to obtain the title acid compound as a pale yellow-orange glass melting below 50° C.

Example 12

Preparation of 2,2-Bis(2-methoxyphenyl)-butane 1,1-Bis(2-methoxyphenyl)ethene (5.6 g) was dissolved in 25 ml of tetrahydrofuran and 25 ml of a 1.3M solution of methyl lithium in ether was added dropwise with stirring. The solution became dark red and exothermed. After 2 hours, 5.0 ml of methyl iodide was added slowly with stirring. The solution again exothermed. When all of the methyl iodide had been added the starting material was found to be completely consumed and replaced by a single product by gas-liquid chromatography. About 300 ml of ether was added and the resulting solution was extracted with 100 ml of water and then 100 ml of brine, dried over magnesium sulfate, filtered, and concentrated by evaporation under reduced pressure to obtain 5.46 g (88 percent of theory) of the title compound as a pale yellow crystalline solid melting at 49°–52° C. The proton and carbon NMR and infrared spectra were consistent with the assigned structure.

Elemental analysis: Calc. for $C_{18}H_{22}O_2$: % C, 80.0; % H, 8.20. Found: % C, 80.3; % H, 8.09.

Example 13

Preparation of 12-Ethyl-12-methyl-12H-dibenzo[d,g][1,3]dioxocin-6-carboxylic Acid and Methyl 12-Ethyl-12-methyl-12H-dibenzo[d,g][1,3]dioxocin-6-carboxylate.

2,2-Bis(2-hydroxyphenyl)butane in impure form was condensed with dichloroacetic acid as in Example 3 to obtain the title acid in impure form. This was esterified with methanol by the procedure of Example 4 to obtain a mixture of 2 isomers of the title ester in an approximately 1:1.5 ratio as determined by gas-liquid chromatography. This was column chromatographed eluting with a 90:10 mixture of hexane and ether to obtain a small fraction that was about 95 percent one isomer and a larger fraction that was a 1:1 mixture of cis/trans isomers. Both fractions were oils. The two fractions obtained were separately hydrolyzed to the title acid using the procedure of Example 3. The single isomer fraction gave a single isomer of the title acid as an oil which crystallized from ether-hexane on standing in an open dessicator and melted at 123°–124° C. The mixed isomer fraction gave a 1:1 mixture of the isomers of the title acid as a glassy solid melting at about 80°–85° C. The proton NMR and infrared spectra of both products were consistent with the assigned structures, including the isomer distribution.

Elemental analysis: Calc. for $C_{18}H_{18}O_4$: % C, 72.5; % H, 6.08. Found(single isomer): % C, 72.4; % H, 6.15. Found(1:1 isomer mix): % C, 72.2; % H, 5.87.

Example 14

Preparation of 1,1-Bis(2-hydroxyphenyl)ethanol

A solution of 10.71 g of 2,2'-dihydroxybenzophenone in 100 ml of ether was prepared and added slowly with stirring to 76 ml of an ice-bath cooled 3.0M solution of methyl magnesium bromide in ether. The ice bath was removed and the mixture was allowed to react for another hour at ambient temperature and then it was heated at reflux for 2 hours. The reaction was quenched with 100 ml of saturated aqueous ammonium chloride, diluted with 100 ml of ether, and the phases separated. The aqueous phase was extracted with 2-100 ml portions of ether. The organic phase and ether extracts were combined and extracted with saturated aqueous ammonium chloride, dried over magnesium sulfate, filtered, and concentrated by evaporation under reduced pressure to obtain a yellow solid. This was recrystallized from an ether-hexane mixture to obtain 10.06 g (94 percent of theory) of the title compound as light yellow crystals. The proton NMR spectrum was consistent with the assigned structure.

Elemental analysis: Calc. for $C_{14}H_{14}O_3$: % C, 73.0; % H, 6.13. Found: % C, 73.0; % H, 6.23.

1,1-Bis(2-hydroxyphenyl)propanol was prepared similarly using ethyl magnesium bromide.

Example 15

Preparation of 1,1-Bis(2-hydroxyphenyl)-ethane 1,1-Bis(2-hydroxyphenyl)ethanol (8.57 g) dissolved in 40 ml of dichloromethane was cooled with an ice bath and to this was added sequentially with stirring 3.70 ml of trifluoroacetic acid in 20 ml of dichloromethane and (dropwise) 7.67 ml of triethylsilane in 20 ml of dichloromethane. The mixture was allowed to warm to room temperature and react for another 2 hours. Ether and water were added and the phases separated. The organic phase was extracted with several small portions of 2N sodium hydroxide and the extracts were combined and acidified with hydrochloric acid. The resulting mixture was extracted with ether and the ether extract was dried over magnesium sulfate, filtered, and concentrated by evaporation under reduced pressure to obtain 6.10 g of the title compound as a brown oil.

1,1-Bis(2-hydroxyphenyl)propane was prepared similarly from 1,1-bis(2-hydroxyphenyl)propanol and 1-(3-chloro-2-methoxy-methoxyphenyl)-1-(2-methoxyphenyl)ethane was prepared similarly from 1-(3-chloro-2-methoxymethoxyphenyl)-1-(2-methoxyphenyl)ethanol.

Example 16

Preparation of Methyl 12-Methyl-12H-dibenzo[d,g][1,3]dioxocin-6-carboxylate 1,1-Bis(2-hydroxyphenyl)ethane was treated with dichloroacetic acid, potassium carbonate, and potassium iodide in isopropyl alcohol as in Example 3 and the product obtained was esterified with methanol as in Example 4 to obtain 1.71 g of the title compound as a mixture of cis and trans isomers. A portion of this was recrystallized from ether to obtain a pure sample of the cis isomer of the title compound as a white solid melting at 146°–147° C. The geometry was determined by proton NMR spectroscopy.

Elemental analysis: Calc. for $C_{17}H_{16}O_4$: % C, 71.8; % H, 5.67. Found: % C, 71.5; % H, 5.77.

Methyl 12-ethyl-12H-dibenzo[d,g][1,3]dioxocin-6-carboxylate was prepared similarly from 1,1-bis(2-hydroxyphenyl)propane. A 1:1 mixture of cis and trans isomers was obtained as a white solid melting at 134.5°–135.5° C. after recrystallization with methylcyclohexane. The assigned structure was consistent with the proton NMR spectrum Elemental analysis: Calc. for $C_{18}H_{18}O_4$: % C, 72.5; % H, 6.08. Found: % C, 72.6; % H, 5.95.

Example 17

Preparation of 12-Ethyl-12H-dibenzo[d,g][1,3]dioxocin-6-carboxylic Acid

Methyl 12-ethyl-12H-dibenzo[d,g][1,3]dioxocin-6-carboxylate as a 1:1 mixture of isomers (1.25 g) was hydrolyzed as in Example 3 to obtain the title compound (as a 1:1 mixture of cis and trans isomers) as an off-white solid melting at 142°–145° C. The assigned structure was consistent with the proton NMR spectrum.

Elemental analysis: Calc. for $C_{17}H_{16}O_4$: % C, 71.8; % H, 5.67. Found: % C, 71.1; % H, 5.50.

Example 18

Preparation of 1-(3-Chloro-2-methoxymethoxyphenyl)-1-(2-methoxyphenyl)ethanol

1-Chloro-2-methoxymethoxybenzene (20.0 g) was combined with 72.5 ml of 1.6M n-butyl lithium in hexane at 0° C. with stirring and allowed to react for 4 hours. A solution of 16.0 ml of 2-methoxyacetophenone in 20 ml of tetrahydrofuran was then added with stirring. After a short reaction period, water and ether were added and the ether layer was dried over magnesium sulfate, filtered, and concentrated by evaporation under reduced pressure to obtain an oil. This was purified by liquid chromatography, eluting with a 95:5 mixture of hexane and ethyl acetate, to obtain 6.67 g of the title compound as an oil. The assigned structure was consistent with the proton NMR spectrum.

Example 19

Preparation of Methyl 2-Chloro-12-methyl-12H-dibenzo[d,g][1,3]dioxocin-6-carboxylate 1-(3-Chloro-2-hydroxyphenyl)-1-(2-hydroxyphenyl)ethane was condensed with dichloroacetic acid as in Example 3 to obtain the acid of the title compound in impure form. This was esterified with methanol by the procedure of Example 4 to obtain a mixture of cis and trans isomers of the title compound. The mixture was liquid chromatographed to obtain one fraction identified as the trans isomer melting at 144°–145° C. and a second fraction containing an approximately 3.7:1 ratio of the isomers melting at 124°–136° C. The assigned structures were consistent with the proton NMR spectra.

Elemental analysis: Calc. for $C_{17}H_{15}O_4Cl$: % C, 64.1; % H, 4.74 Found (trans isomer) % C, 64.1; % H, 4.83. Found (mixed isomers): % C, 64.3; % H, 4.91.

Example 20

Preparation of (2-Methoxyphenyl)-(3-methyl-2-methoxymethoxyphenyl)methanol

1-Methyl-2-methoxymethoxybenzene (15.2 g) was added to a mixture of 75 ml of a 1.6M solution of n-butyl lithium in hexane and 18.1 ml of tetramethylethylenediamine at 0° C. with stirring. After 4 hours, 13.6 g of o-anisaldehyde dissolved in 30 ml of tetrahydrofuran was added. The mixture was allowed to react for 0.5 hour and was then poured into a mixture of ice and saturated aqueous ammonium chloride. The resulting mixture was extracted with ether and the ether extract was dried over magnesium sulfate, filtered, and concentrated by evaporation under reduced pressure to obtain 39.5 g of the title compound as an off-white solid. The assigned structure was consistent with the proton NMR spectrum.

Example 21

Preparation of 2-Methoxymethoxy-3-methyl-2'-methoxybenzophenone

A solution of 8.72 ml of oxalyl chloride in 300 ml of dichloromethane was cooled with a dry ice-acetone bath and a solution of 13.9 ml of dimethyl sulfoxide in 50 ml of dichloromethane was added dropwise with stirring. After 30 min, (2-methoxyphenyl)(3-methyl-2-methoxymethoxyphenyl)methanol (26.4 g) dissolved in 100 ml of dichloromethane was added slowly with stirring and the mixture allowed to react for 1 hour. Triethylamine (64 ml) was then added and the resulting mixture was stirred another 30 min cold and then allowed to warm to room temperature. The product mixture was extracted sequentially with water, 5 percent hydrochloric acid, water, and 5 percent sodium carbonate. It was then dried over magnesium sulfate, filtered, and concentrated by evaporation under reduced pressure to obtain an oil. This was purified by preparative liquid chromatography to obtain the title compound as an oil. The assigned structure was consistent with the proton NMR spectrum.

Example 22

Preparation of 1-(2-Methoxymethoxy-3-methyl)-1-(2-methoxyphenyl)-cyclopropane

2-Methoxymethoxy-3-methyl-2'-methoxybenzophenone (17.5 g) was combined with the sodium salt of triethyl phosphonoacetate (2.2 equivalents) in 250 ml of dimethoxyethane and the mixture heated at reflux with stirring for 2 days. Water and ether were added and the organic phase was separated, extracted with water, dried over magnesium sulfate, filtered, and concentrated by evaporation under reduced pressure to obtain an oil. This was purified by preparative liquid chromatography, eluting with a 90:10 mixture of hexane and acetone, to obtain ethyl 3-(2-methoxyphenyl)-3-(2-methoxymethoxy-3-methylphenyl)propenoate as an intermediate consisting of a mixture of isomers. The assigned structure was consistent with the proton NMR spectrum. This was dissolved in 50 ml of tetrahydrofuran and treated with 61 ml of a solution of 1M lithium aluminum hydride in tetrahydrofuran at ambient temperature with stirring. The mixture was heated at reflux with stirring for 4 hours. It was then allowed to cool, was quenched with 10 percent sulfuric acid, and was diluted with ether. The organic phase was separated, extracted with water, dried over magnesium sulfate, filtered, and concentrated by evaporation under reduced pressure to obtain a crude product. This was purified by preparative liquid chromatography, eluting with a 95:5 mixture of hexane and acetone, to obtain 6.01 g of the title compound as a gum. The assigned structure was consistent with the proton NMR spectrum.

Example 23

Preparation of Methyl 4'-Methylspiro(cyclopropane-1,12'(12'H)-dibenzo[d,g][1,3]dioxocin)-6'-carboxylate 1-(3-Methyl-2-hydroxyphenyl)-1-(2-hydroxyphenyl)-cyclopropane was condensed with dichloroacetic acid as in Example 3 to obtain the acid of the title compound in impure form. This was esterified with methanol by the procedure of Example 4 to obtain the title compound in impure form. This was purified by liquid chromatography, eluting with a 90:10 mixture of hexane and acetone to obtain 1.29 g of the title compound as a white crystalline solid melting at 98°-99° C. The assigned structure was consistent with the proton and carbon NMR and infrared spectra.

Elemental analysis: Calc. for $C_{19}H_{18}O_4$; % C, 73.5; % H, 5.85. Found: % C, 71.2; % H, 5.84.

Example 24

Preparation of (3-Chloro-2-methoxymethoxyphenyl)(2-methoxymethoxyphenyl)methanol A 1.6M solution of n-butyl lithium in hexane (140 ml) was placed in a 1 l flask and cooled in an ice bath. To this was added with stirring 34 ml of tetramethylethylenediamine and, after a 10 min reaction period, 34.5 g of 1-chloro-2-methoxymethoxybenzene (dropwise over a 30 min period). A pale orange suspension formed and this was stirred for 4 hours continuing the ice bath cooling. A solution of 34.5 g of 2-methoxymethoxybenzaldehyde in 30 ml of tetrahydrofuran was added with stirring and cooling. The reaction was exothermic. When the addition was complete, the mixture was allowed to warm to room temperature and was then quenched carefully with water. The resulting mixture was poured into a mixture of 1 l of ethyl acetate and 500 ml of aqueous ammonium chloride. The phases were separated and the organic phase was extracted twice with water and once with brine, dried over magnesium sulfate, filtered, and concentrated by evaporation under reduced pressure to obtain a viscous, pale orange oil. This was purified by filtration chromatography, eluting with mixtures of hexane and dichloromethane starting with pure hexane and ending with pure dichloromethane, to obtain 52.2 g (77 percent of theory) of the title compound as a pale yellow oil. The proton and carbon NMR and infrared spectra were consistent with the assigned structure.

Elemental analysis:
Calc. for $C_{17}H_{19}ClO_5$: % C, 60.3; % H, 5.65. Found: % C, 60.6; % H, 5.57.

(3-Methoxy-2-methoxymethoxyphenyl)(2-methoxymethoxyphenyl)methanol (33.7 g) was prepared similarly from 33.6 g of 2-methoxyphenol and 33.2 g of 2-methoxymethoxybenzaldehyde and characterized by proton NMR spectroscopy.

Example 25

Preparation of 3-Chloro-2-methoxymethoxy-2'-methoxymethoxybenzophenone

A solution of 16.0 ml of oxalyl chloride in 500 ml of dichloromethane was placed in a 1 l flask and cooled with a dry ice-acetone bath. Dimethyl sulfoxide (14.0 ml) was added dropwise with stirring over a 10 min period. After a 40 min reaction period, a solution of 51.0 g of (3-chloro-2-methoxymethoxyphenyl)(2-methoxymethoxyphenyl)methanol in 120 ml of dichloromethane was added dropwise over a 45 min period with stirring at about −78° C. and allowed to react another 45 min. An orange suspension formed. Triethylamine (50 ml) was added and the slurry was swirled occasionally and was allowed to warm to room temperature. The slurry was diluted with 1 l of ether and the resulting mixture was extracted with 3-300 ml portions of water, 300 ml of 2 percent hydrochloric acid, and 200 ml of saturated aqueous sodium bicarbonate, dried over magnesium sulfate, filtered, and concentrated by evaporation under reduced pressure to obtain 50.5 g of the title compound as a viscous pale orange-tinted oil. The proton and carbon NMR spectra were consistent with the assigned structure.

3-Methoxy-2-methoxymethoxy-2'-methoxymethoxybenzophenone was prepared similarly from (3-methoxy-2-methoxymethoxyphenyl)(2-methoxymethoxyphenyl)methanol and characterized by proton NMR spectroscopy.

Example 26

Preparation of 1-(3-Chloro-2-methoxymethoxyphenyl)-1-(2-methoxymethoxyphenyl)ethene A 1.0M solution of trimethylsilylmethyl lithium in pentane (160 ml) was added with stirring to a solution of 50.5 g of 3-chloro-2-methoxymethoxy-2'-methoxymethoxybenzophenone in 500 ml of tetrahydrofuran over a 45 min period. There was a mild exotherm. Analysis by gas-liquid chromatography indicated the reaction was incomplete so another 10 ml of the trimethylsilylmethyl lithium solution was added. After a 20 min reaction period 7.3 g of potassium t-butoxide were added and the reaction was heated to reflux with a heating mantle and held there for 40 min. The mixture was then allowed to cool and was diluted with 1 l of ether. The ethereal solution was extracted with 6-300 ml portions of water and 200 ml of brine, dried over magnesium sulfate, filtered, and concentrated by evaporation under reduced pressure to obtain 50.2 g of the title compound as a pale orange oil. The proton NMR spectrum was consistent with the assigned structure.

1-(3-Methoxy-2-methoxymethoxyphenyl)-1-(2-methoxymethoxyphenyl)ethene was prepared similarly from 3-methoxy-2-methoxymethoxy-2'-methoxymethoxybenzophenone and characterized by proton NMR spectroscopy.

Example 27

Preparation of 1-(3-Chloro-2-methoxymethoxyphenyl)-1-(2-methoxymethoxyphenyl(cyclopropane Phenylthiomethyl lithium was prepared by adding 120 ml of 2.5M butyl lithium in hexane to a solution of 37.3 g of thioanisole and 33.7 g of 1,4-diazabicyclo[2,2,-2]octane in 400 ml of tetrahydrofuran dropwise with stirring at 0° C. and then allowing the mixture to react for 45 min at 0° C. and 1 hour at room temperature. A solution of 50.2 g of 1-(3-chloro-2-methoxymethoxyphenyl)-1-(2-methoxymethoxyphenyl)ethene dissolved in 100 ml of tetrahydrofuran was added slowly to this at ambient temperature with stirring. A brick red color developed. The mixture was heated to reflux for about 30 min. Analysis by gas-liquid chromatography indicated that the reaction was complete. The mixture was cooled, diluted with ether, and quenched with water. The solution was extracted several times with water and once with brine, dried over magnesium sulfate, filtered, and concentrated by evaporation under reduced pressure to obtain about 80 ml of a pale orange oil. This was subjected to a bulb-to-bulb distillation at up to 120° C. and 0.3 mm of mercury pressure. The thioanisole impurity was removed and a product cut of less than 5 ml was collected. Considerable decomposition took place. The product cut was partially purified by liquid chromatography, eluting with a 95:5 mixture of hexane and ether to obtain 1.8 g of the title compound of about 82 percent purity (gas-liquid chromatography) as a viscous oil. The proton NMR spectrum was consistent with the assigned structure.

1-(3-Methoxy-2-methoxymethoxyphenyl)-1-(2-methoxymethoxyphenyl)cyclopropane was prepared similarly from (1-(3-methoxy-2-methoxymethoxyphenyl)-1-(2-methoxymethoxyphenyl)ethene and characterized by proton NMR spectroscopy.

Example 28

Preparation of 1-(3-Chloro-2-hydroxyphenyl)-1-(2-hydroxyphenyl)cyclopropane

A catalytic amount (0.05 g) of p-toluenesulfonic acid was added to a solution of 1.8 g of impure 1-(3-chloro-2-methoxymethoxyphenyl)-1-(2-methoxymethoxyphenyl)cyclopropane in 45 ml of methanol and the mixture heated at reflux with stirring for 1 hour. It was then concentrated by evaporation under reduced pressure and diluted with 120 ml of ethyl acetate. The resulting solution was extracted with saturated aqueous sodium bicarbonate, dried over magnesium sulfate, filtered, and concentrated by evaporation under reduced pressure to obtain 1.45 g of a viscous oil. This was found by proton NMR analysis to retain some methoxymethoxy groups so the procedure was repeated, this time refluxing for 2.5 hours. The title compound was obtained as a beige solid amounting to 1.41 g. The proton and carbon NMR spectra were consistent with the assigned structure.

1-(3-Methoxy-2-hydroxyphenyl)-1-(2-hydroxyphenyl)cyclopropane was prepared similarly from 1-(3-methoxy-2-methoxymethoxyphenyl)-1-(2-methoxymethoxy-phenyl)cyclopropane and characterized by proton NMR spectroscopy.

Example 29

Preparation of Methyl 4'-Chlorospiro(cyclopropane-1,12'(12'H)-dibenzo[d,g][1,3]dioxocin)-6'-carboxylate.

1-(3-Chloro-2-hydroxyphenyl)-1-(2-hydroxyphenyl)cyclopropane was condensed with dichloroacetic acid as in Example 3 to obtain the acid of the title compound in impure form. This was esterified with methanol by the procedure of Example 4 to obtain the title compound in impure form. This was twice purified by liquid chromatography, eluting with a 90:10 mixture of hexane and ether, and crystallizing from hexane to obtain as a first crop 0.30 g of the title compound as a white crystalline solid melting at 105°-111° C. A second crop of about 94 percent purity was also obtained. The proton and carbon NMR spectra were consistent with the assigned structure.

Elemental analysis: Calc. for $C_{18}H_{15}ClO_4$ % C, 65.4; % H, 4.57. Found: % C, 64.7; % H, 4.61.

Example 30

Preparation of 4'-Chlorospiro(cyclopropane-1,12'(12'H)-dibenzo[d,g][1,3]dioxocin)-6'-carboxylic Acid.

Methyl 4'-chlorospiro(cyclopropane-1,12'(12'H)-dibenzo[d,g][1,3]dioxocin)-6'-carboxylate was hydrolyzed using the procedure of Example 4. The crude product was purified by recrystallization from an ether/hexane mixture to obtain the title compound as white granules melting at 154°-158° C. The proton and carbon NMR spectra were consistent with the assigned structure.

Elemental analysis: Calc. for $C_{17}H_{13}ClO_4$: % C, 64.5; % H, 4.14. Found: % C, 64.4; % H, 4.06.

Example 31

Preparation of Methyl 4'-Methoxyspiro(cyclopropane-1,12'(12'H)-dibenzo[d,g][1,3]dioxocin)-6'-carboxylate 1-(3-Methoxy-2-hydroxyphenyl)-1-(2-hydroxyphenyl)cyclopropane was condensed with dichloroacetic acid as in Example 3 to obtain the acid of the title compound in impure form. This was esterified with methanol and purified by the procedure of Example 4 to obtain the title compound as a white crystalline solid melting at 140°–141° C. The proton NMR and infrared spectra were consistent with the assigned structure.

Elemental analysis: Calc. for $C_{19}H_{18}O_5$: % C, 69.9; % H, 5.56. Found: % C, 69.8; % H, 5.54.

Example 32

Preparation of (2-Methoxymethoxyphenyl)-(3,4-dimethoxy-2-methoxymethoxyphenyl)methanol A 1.6M solution of butyl lithium in hexane (91 ml, 146 mmol) was placed in an oven-dried 500 ml 3-necked flask and cooled to 0° C. and then 22.5 ml (20.1 mmol) of tetramethylethylenediamine was added with stirring. After a 10 min reaction period, a solution of 18.3 g (133 mmol) of methoxymethoxybenzine was added and the mixture allowed to stir for about 3.5 hours at 0° C. 3,4-Dimethoxy-2-methoxymethoxybenzaldehyde (30.0 g, 133 mmol) in 18 ml of tetrahydrofuran was then added dropwise with stirring. The mixture was allowed to warm to room temperature and stir for 1 hour and was then quenched with 50 ml of saturated aqueous ammonium chloride. The resulting mixture was extracted with 200 ml of ethyl acetate three times. The combined extracts were dried over magnesium sulfate and concentrated by evaporation under reduced pressure to obtain 48.5 g of an oil. This was purified by silica gel chromatography on an 8 in. diameter sintered glass funnel eluting with mixtures of hexane and dichloromethane increasing from 38 percent to 75 percent dichloromethane to obtain 32.2 g (68 percent of theory) of the title compound as a yellow oil. The proton and carbon NMR and infrared spectra were consistent with the assigned structure.

Elemental analysis: Calc. for $C_{19}H_{24}O_7$: % C, 62.6; % H, 6.41. Found: % C, 62.7; % H, 6.64.

Example 33

Preparation of 2'-Methoxymethoxy-3,4-dimethoxy-2-methoxymethoxybenzophenone

A mixture 12.3 g (126 mmol) of chromium trioxide in 153 ml of dichloromethane was cooled to 0° C. and 20.3 ml (252 mmol) of pyridine were added with stirring to obtain, after 45 min, a yellow-brown solution (Collin's reagent). (2-Methoxymethoxyphenyl) (3,4-dimethoxy-2-methoxymethoxyphenyl)methanol (7.67 g, 21 mmol) was added with stirring and the mixture allowed to warm to room temperature with stirring overnight. Twenty grams of florisil were added and the mixture was concentrated by evaporation under reduced pressure and filtered through celite and then further eluted with ether. The resulting mixture was concentrated under reduced pressure and purified by liquid chromatography using a Waters Prep 500 Chromatograph with a silica gel column and eluting with a 70:30 mixture of hexane and ethyl acetate to obtain 6.0 g (79 percent of theory) of the title compound as an oil. The proton and carbon NMR and infrared spectra were consistent with the assigned structure.

Elemental analysis: Calc. for $C_{19}H_{22}O_7$: % C, 63.0; % H 6.12. Found: % C, 62.9; % H, 5.90.

Example 34

Preparation of 1-(2-Methoxymethoxyphenyl)-1-(3,4-dimethoxy-2-methoxymethoxyphenyl)-ethene A solution of 1.84 g (5.1 mmol) of 2'-methoxymethoxy-3,4-dimethoxy-2-methoxymethylbenzophenone in 17 ml of dry tetrahydrofuran was cooled to 0° C. and 9.1 ml of 1.0M (9.1 mmol) of trimethylsilymethyl lithium in pentane was added with stirring. After 2.5 hours, 0.38 ml (4.1 mmol) of t-butyl alcohol and 231 mg (2.0 mmol) of potassium t-butoxide were added and the mixture was heated at reflux with stirring for 4 hours. The resulting mixture was diluted with 40 ml of ether and the solution obtained was dried over magnesium sulfate and concentrated by evaporation under reduced pressure to obtain 2.0 g of an oil. This was purified by filtration chromatography on a 2 in. bed of silica gel eluting with hexane containing increasing amounts of ether to obtain the title compound as a clear oil. The proton and carbon NMR and infrared spectra were consistent with the assigned structure.

Elemental analysis: Calc. for $C_{20}H_{24}O_6$: % C, 66.7; % H, 6.71. Found: % C, 66.2; % H, 6.56.

Example 35

Preparation of 1-(2-Methoxymethoxyphenyl)-1-(3,4-dimethoxy-2-methoxymethoxyphenyl)-cyclopropane A solution of 5.4 g (44 mmol) of thioanisole and 4.89 g (43.6 mmol) of 1,4-diazabicyclo[2,2,2]-octane in 44 ml of tetrahydrofuran was placed in an oven-dried flask and cooled to 0° C. A 2.5M solution of butyl lithium in hexane (17.4 ml, 43.6 mmol) was added with stirring and the mixture allowed to warm to room temperature and react for about 1 hour to form phenylthiomethyl lithium. A solution of 3.14 g (8.71 mmol) of 1-(2-methoxymethoxyphenyl)-1-(3,4-dimethoxy-2-methoxymethoxyphenyl)ethene in tetrahydrofuran was added and the mixture heated to reflux with stirring under an argon atmosphere. After 10 hours another 21.8 mmol of phenylthiomethyl lithium was prepared and added to the mixture and refluxing was continued overnight. The mixture was then cooled and poured into 200 ml of 5 percent aqueous sodium hypochlorite solution and 200 g of ice and 150 ml of ether added. The organic phase was separated, dried over magnesium sulfate and concentrated by evaporation under reduced pressure to obtain 6.61 g of an oil. This was purified by silica gel chromatography (80 mm × 3" filter funnel), eluting with hexane containing ever increasing amounts of ether to obtain 1.16 g of the title compound as an oil. The proton and carbon NMR and infrared spectra were consistent with the assigned structure.

Elemental analysis: Calc. for $C_{21}H_{26}O_6$: % C, 67.4; % H, 7.00. Found: % C, 65.8; % H, 6.46.

When an initial charge of 3.3 moles of phenylthiomethyl lithium per mole of olefin was employed, the product was 1-(2-methoxymethoxyphenyl)-1-(4-hydroxy-3-methoxy-2-methoxymethoxyphenyl)-cyclopropane, an oil obtained in 33 percent yield and identified by proton NMR spectroscopy.

Example 36

Preparation of 1-(2-Hydroxy-3,4-dimethoxyphenyl)-1-(2-hydroxyphenyl)cyclopropane A solution of 1.16 g (3.1 mmol) of 1-(2-methoxymethoxyphenyl)-1-(3,4-dimethoxy-2-methoxymethoxyphenyl)cyclopropane and 80 mg (0.47 mmol) of p-toluenesulfonic acid in 26 ml of methanol was heated at reflux with stirring for 2 hours under an argon atmosphere. The mixture was concentrated to half by evaporation under reduced pressure and 40 ml of ether was added. The resulting solution was extracted with 30 ml of 5 percent aqueous sodium bicarbonate then 30 ml of water, dried over magnesium sulfate, and concentrated by evaporation under reduced pressure to obtain 880 mg of the title compound as a foamy oil. The proton NMR spectrum was consistent with the assigned structure.

Example 37

Preparation of Methyl 3',4'-Dimethoxyspiro(cyclopropane-1,12'(12'H)-dibenzo[d,g][1,3]dioxocin)-6'-carboxylate 1-(2-Hydroxy-3,4-dimethoxyphenyl)-1-(2-hydroxyphenyl)cyclopropane was condensed with dichloroacetic acid as in Example 3 to obtain the acid of the title compound in impure form. This was esterified with methanol by the procedure of Example 4 to obtain a brown oil. This was purified by flash silica gel chromatography (25 mm×6″), eluting with hexane containing ever increasing amounts of ether to obtain the title compound as a clear oil. The proton and carbon NMR and infrared spectra were consistent with the assigned structure.

Elemental analysis: Calc. for $C_{14}H_{18}O_4$: % C, 67.4; % H, 5.66. Found: % C, 67.7; % H, 5.77.

Example 38

Preparation of 3',4'-Dimethoxyspiro(cyclopropane-1,12'(12'H)-dibenzo[d,g][1,3]dioxocin)-6'-carboxylic Acid A solution of 76 mg (0.23 mmol) of methyl 3',4'-dimethoxyspiro(cyclopropane-1,12'(12'H)-dibenzo[d,g][1,3-]dioxocin)-6'-carboxylate in 0.46 ml of tetrahydrofuran was combined with 0.172 ml (0.35 mmol) of 2N aqueous sodium hydroxide and the mixture stirred for 1.3 hour. The resulting mixture was diluted with 0.5 ml of water, extracted with ether, and then acidified with 1N aqueous hydrochloric acid. The resulting mixture was extracted 3 times with 1 ml portions of ether and the combined ethereal extracts were dried over magnesium sulfate and concentrated by evaporation under reduced pressure to obtain the title compound in quantitative yield as a white solid. The proton and carbon NMR and infrared spectra were consistent with the assigned structure.

Elemental analysis: Calc. for $C_{19}H_{18}O_6$: % C, 66.7; % H, 5.30. Found: % C, 67.2; % H, 5.04.

Example 39

Preparation of (2-Methoxymethoxyphenyl)-(2-methoxy-4-methylphenyl)methanol

The general procedure of Example 31 was followed using 2-methoxy-4-methylbenzaldehyde as the aldehyde. The title compound was obtained as a yellow oil in 77 percent yield. The proton and carbon NMR and infrared spectra were consistent with the assigned structure.

Elemental analysis: Calc. for $C_{17}H_{20}O_4$: % C, 70.9; % H, 6.99. Found: % C, 70.8; % H, 6.75.

Example 40

Preparation of 2'-Methoxymethoxy-2-methoxy-4-methylbenzophenone

The general procedure of Example 32 was followed using (2-methoxymethoxyphenyl) (2-methoxy-4-methylphenyl)methanol and the product purified by liquid chromatography in a similar manner to obtain the title compound as an oil in 85 percent yield. The proton and carbon NMR and infrared spectra were consistent with the assigned structure.

Elemental analysis: Calc. for $C_{17}H_{18}O_4$: % C, 71.3; % H, 6.34. Found: % C, 71.8; % H, 6.36.

Example 41

Preparation of 1-(2-Methoxymethoxyphenyl)-1-(4-methyl-2-methoxyphenyl)ethene The general procedure of Example 33 was followed using 2'-methoxymethoxy-2-methoxy-4-methylbenzophenone and the product was purified similarly to obtain the title compound as a clear oil. The proton and carbon NMR and infrared spectra were consistent with the assigned structure.

Elemental analysis: Calc. for $C_{20}H_{24}O_6$ % C, 76.0; % H, 7.09 Found % C, 73.4; % H, 7.32

Example 42

Preparation of 1-(2-Methoxymethoxyphenyl)-1-(4-methyl-2-methoxyphenyl)cyclopropane The general procedure of Example 34 was followed using 1-(2-methoxymethoxyphenyl)-1-(4-methyl-2-methoxyphenyl)ethene and, initially, 3.3 moles of phenylthiomethyl lithium reagent per mole of olefin. The title compound was obtained as a clear oil in 44 percent yield and its structure was verified by proton NMR spectroscopy.

Example 43

Preparation of 1-(2-Hydroxyphenyl)-1-(2-hydroxy-4-methylphenyl)cyclopropane

A solution prepared from 490 mg (1.64 mmol) of 1-(2-methoxymethoxyphenyl)-1-(2-methoxy-4-methylphenyl)cyclopropane and 6.1 ml of a 1M solution (8.2 mmol) of bromodiethylborane in dichloromethane was stirred overnight under an argon atmosphere. Ten ml of water were added, the phases were separated, and the aqueous phase was extracted twice with 20 ml of dichloromethane. The combined organic extracts were dried over magnesium sulfate and concentrated by evaporation under reduced pressure to obtain 1-(2-hydroxyphenyl)-1-(2-methoxy-4-methylphenyl)cyclopropane. The proton NMR spectrum was consistent with the assigned structure. This was dissolved in 0.8 ml (8.2 mmol) of a 5M solution of bromodimethylborane and allowed to stir overnight. Nothing happened. The mixture was cooled to 0° C. and 3.3 ml (3.3 mmol) of a 1M solution of boron tribromide was added with stirring under an argon atmosphere. After a short reaction period 2 ml of water was added and the mixture was extracted with 2 ml of 5 percent aqueous sodium bicarbonate then with 2 ml of water, dried over magnesium sulfate and concentrated by evaporation under reduced pressure to obtain 350 mg (84 percent of theory) of the title compound as a foamy brown oil. The proton and carbon NMR spectra were consistent with the assigned structure.

Example 44

Preparation of Methyl 3'-Methylspiro(cyclopropane-1,12'(12'H)-dibenzo[d,g][1,3]dioxocin)-6'-carboxylate 1-(2-Hydroxy-4-methylphenyl)-1-(2-hydroxyphenyl)-cyclopropane was condensed with dichloroacetic acid as in Example 3 to obtain the acid of the title compound in impure form. This was esterified with methanol by the procedure of Example 4 to obtain a hemi-hydrate of the title compound. The proton and carbon NMR and infrared spectra were consistent with the assigned structure.

Elemental analysis: Calc. for $C_{19}H_{18}O_4 \cdot \frac{1}{2}H_2O$: % C, 71.4; % H, 6.0. Found: % C, 71.0; % H, 5.7.

Example 45

Preparation of 3'-Methylspiro(cyclopropane-1,12'(12'H)-dibenzo[d,g][1,3]dioxocin)-6'-carboxylic Acid Methyl 3'-methylspiro(cyclopropane-1,12'(12'H)-dibenzo[d,g][1,3]dioxocin)-6'-carboxylate was hydrolyzed by the method of Example 37 to obtain the title compound as a white solid. The proton and carbon NMR spectra were consistent with the assigned structure.

Example 46

Postemergence Herbicidal Activity

Compounds of the invention were dissolved in a mixture of 14 ml acetone and 1 ml of dimethyl sulfoxide at one half of the most concentrated desired application concentration and the resulting solution was combined with 15 ml of an aqueous mixture containing about 20 percent isopropyl alcohol, about 2 percent Atplus 411F crop oil concentrate, and about 0.04 percent Triton X-155® surfactant. Solutions containing lower concentrations were prepared by diluting this mixture with a solution containing equal parts of a mixture of the second component described above and acetone containing 3 percent dimethyl sulfoxide. The solutions of known concentration were sprayed evenly onto various greenhouse-grown plant species to obtain total coverage in approximately the 2–4 leaf stage by means of a hand sprayer. The treated plants and control plants were placed in a greenhouse and held under conditions conductive to growth. After 13 days the percentage of control compared to the untreated plants was determined visually. Representative compounds tested, application rates employed, plant species tested, and results are given in Table II. The control is stated on a scale of 0 to 100 with 100 corresponding to complete kill and 0 to no effect. In this test an application of about 100 ppm results in an application of about 260 g/Ha.

TABLE II

POSTEMERGENCE CONTROL OF INDICATED SPECIES AT INDICATED DOSE RATES

| Cpd No. | Dose, ppm | Coffee-weed | Cockle-bur | Jimson-weed | Lamium | Morning-glory | Pig-weed | Velvet-leaf | Wild Buck-wheat | Johnson-grass | Wild Oats | Yellow Foxtail | Yellow Nut-sedge |
|---|---|---|---|---|---|---|---|---|---|---|---|---|---|
| 1 | 500 | 100 | 80 | 95 | 100 | 90 | 90 | 75 | 100 | 50 | 75 | 75 | 80 |
| 3 | 500 | 100 | 90 | 100 | 90 | 80 | 100 | 40 | 85 | 50 | 80 | 0 | 70 |
| 4 | 500 | 100 | 100 | 100 | 100 | 100 | 100 | 50 | 75 | 50 | 70 | 40 | 80 |
| 8 | 500 | 100 | 100 | 100 | 85 | 90 | 85 | 100 | 90 | 70 | 70 | 0 | 50 |
| 13 | 1000 | 50 | 0 | 50 | — | 40 | 50 | 0 | 60 | 0 | — | 0 | 0 |
| 14 | 2000 | 50 | 60 | 50 | — | 70 | 60 | 20 | 35 | 45 | — | 30 | 0 |
| 16 | 1000 | 95 | 30 | 90 | — | 30 | 70 | 100 | 40 | 0 | 0 | 45 | 0 |
| 20 | 125 | 100 | 100 | 100 | 75 | 100 | — | 80 | — | — | 70 | 50 | 80 |
| 21 | 62.5 | 100 | 100 | 85 | — | 90 | 70 | 60 | 30 | 60 | 75 | 0 | 80 |
| 22 | 125 | 100 | 100 | 90 | — | 75 | 80 | 75 | 0 | 50 | 90 | 25 | 90 |
| 23 | 250 | 90 | 100 | 100 | 95 | 85 | 95 | 85 | 50 | 75 | 90 | 45 | 80 |
| 26 | 500 | 100 | 100 | 90 | 90 | 90 | 100 | 90 | 100 | 60 | — | 0 | 80 |
| 27 | 2000 | 70 | 20 | 30 | 40 | 50 | 50 | 70 | 50 | 0 | 0 | 0 | 50 |
| 29 | 1000 | 100 | 90 | 90 | 90 | 100 | 85 | 100 | 85 | 100 | 50 | 0 | 85 |
| 31 | 250 | 100 | 95 | 100 | — | 85 | 80 | 100 | 90 | 100 | — | 60 | 75 |
| 33 | 500 | 60 | 70 | 50 | 70 | 75 | 90 | 70 | 95 | 25 | 0 | 50 | 0 |
| 35 | 2000 | 90 | 70 | 70 | 75 | 40 | 50 | 85 | 25 | 30 | 0 | 25 | 0 |
| 44 | 250 | 100 | 80 | 90 | 0 | 50 | 50 | 80 | 50 | 0 | 0 | 0 | 60 |

Example 47

Preemergence Herbicidal Activity.

Compounds of the invention were dissolved in 15 ml of acetone at one half of the most concentrated desired application concentration and the resulting solution was combined with an equal volume of water containing 0.1 percent of Tween® 20 surfactant. Solutions containing lower concentrations were prepared by diluting this with additional aqueous surfactant solution. The seeds of a number of species of plants were planted in beds containing a loam agricultural soil and, after planting, predetermined amounts of the herbicide mixtures were sprayed on the soil surface and watered in to achieve the desired application rates. These and untreated control plants were then placed in a greenhouse under conditions conductive to germination and growth for a period of 14 days at which time a visual assessment was made of the reduction in stand and growth for the treated plants as compared to the control plants. Representative compounds tested, application rates employed, plant species tested, and results are given in Table III. The control is stated on a scale of 0 to 100 with 100 corresponding to complete kill and 0 to no effect.

TABLE III

PREEMERGENCE CONTROL OF INDICATED SPECIES AT INDICATED DOSE RATES

| Cpd No. | Dose, lb/A | Curly Dock | Jimson Weed | Morning-glory | Pig-weed | Velvet-leaf | Cheat Grass | Johnson-grass | Yellow Foxtail | Yellow Nut-sedge |
|---|---|---|---|---|---|---|---|---|---|---|
| 1 | 4.0 | 25 | 90 | 60 | 85 | 80 | 70 | — | 40 | 95 |
| 4 | 2.0 | — | 85 | 75 | 100 | 80 | 95 | 50 | 40 | 100 |
| 8 | 1.0 | 100 | 90 | 90 | 100 | 90 | 95 | 88 | 55 | 100 |
| 19 | 0.25 | 90 | 90 | 95 | 90 | 95 | 60 | 97 | 0 | 100 |
| 20 | 0.25 | 85 | 90 | 90 | 85 | 50 | 75 | 85 | 35 | 85 |
| 22 | 0.25 | 90 | 95 | 95 | 95 | 70 | 95 | 90 | 0 | 100 |
| 25 | 0.25 | 80 | 80 | 93 | 95 | 93 | 70 | 80 | 0 | 100 |
| 29 | 0.50 | 90 | 99 | 85 | 90 | 90 | 90 | 88 | 0 | 100 |

What is claimed is:

1. A method of controlling undesirable vegetation which comprises contacting the vegetation or the locus thereof with a dibenzo[d,g][1,3]-dioxocin-6-carboxylic acid compound of the formula

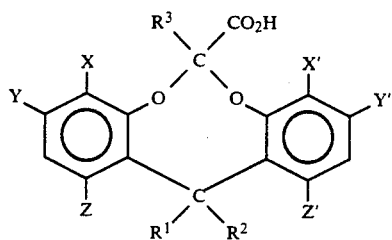

wherein $R^1$ and $R^2$ together represent the fragment $-CH_2CH_2-$;

$R^3$ represents H or $CH_3$; and

X, X', Y, Y', Z, and Z' each, independently represent H, F, Cl, Br, I, CN, $NO_2$, $CO_2H$, $NH_2$, $C_1-C_4$ alkyl, $C_1-C_4$ alkoxy, phenoxy, ($C_1-C_4$ alkylthio, phenylthio, $C_1-C_4$ mono- or dialkylamino, $C_1-C_3$ alkyl)carbonyl, phenylcarbonyl, $C_1-C_4$ alkoxycarbonyl, or $C_1-C_4$ mono- or dialkylaminocarbonyl, wherein each alkyl, alkoxy, and alkylthio group is optionally substituted with one or more compatible groups selected from $C_1-C_4$ alkoxy, $C_1-C_4$ alkylthio, F, Cl, Br, CN, and phenyl and wherein each phenyl group is optionally substituted with up to 3 groups selected from F, Cl, Br, CN, $CF_3$, $C_1-C_4$ alkyl, and $C_1-C_4$ alkoxy;

or an agriculturally acceptable salt, ester, or amide thereof.

2. A method of claim 1 wherein the vegetation is contacted postemergently.

3. A method of claim 1 wherein $R^3$ represents hydrogen.

4. A method of claim 1 wherein X, X', Y, Y', Z, and Z' each independently represent H, F, Cl, Br, $CH_3$, $OCH_3$, $SCH_3$, $CF_3$, or $OC_6H_5$.

5. A method of claim 1 wherein at least one of X and X' represents a designated substituent other than hydrogen.

6. A method of claim 1 wherein the compound is in the form of an agriculturally acceptable salt, ester, or amide.

7. A method of claim 6 wherein the compound is in the form of an agriculturally acceptable ester.

8. A method of claim 7 wherein the ester is a $C_1-C_8$ alkyl or $C_3-C_8$ alkenyl ester, each substituted with up to 3 groups selected from $C_1-C_4$ alkoxy, F, Cl, Br, and phenyl, or a phenyl ester optionally substituted with up to 3 groups selected from F, Cl, Br, $CH_3$, or $CF_3$.

9. A method of claim 8 wherein the ester is a $C_1-C_4$ alkyl ester.

10. A method of claim 9 wherein the ester is a methyl ester.

11. A method of claim 6 wherein the compound is in the form of an agriculturally acceptable salt.

12. A method of claim 11 wherein the compound is in the form of a sodium, potassium, ammonium, dimethylammonium, or triethylammonium salt.

13. A method of claim 4 wherein the compound is spiro(cyclopropane-1,12'(12'H)-dibenzo[d,g][1,3]-dioxocin)-6'-carboxylic acid or an agriculturally acceptable ester, amide, or salt thereof.

14. A method of claim 13 wherein the compound is methyl spiro(cyclopropane-1,12'(12'H)-dibenzo-[d,g][1,3]dioxocin)-6'-carboxylate.

15. A method of claim 5 wherein the compound is methyl 4'-chlorospiro(cyclopropane-1,12'(12'H)-dibenzo[d,g][1,3]dioxocin)-6'-carboxylic acid or an agriculturally acceptable ester, amide, or salt thereof.

16. A method of claim 15 wherein the compound is methyl 4'-chlorospiro(cyclopropane-1,12'(12'H)-dibenzo[d,g][1,3]dioxocin)-6'-carboxylate.

17. A method of claim 5 wherein the compound is 4'-methylspiro(cyclopropane-1,12'(12H)-dibenzo-[d,g][1,3]dioxocin)-6'-carboxylic acid or an agriculturally acceptable ester, amide, or salt thereof.

18. A method of claim 17 wherein the compound is methyl 4'-methylspiro(cyclopropane-1,12'(12'H)-dibenzo[d,g][1,3]dioxocin)-6'-carboxylate.

* * * * *